(12) United States Patent
Pikal et al.

(10) Patent No.: US 10,512,674 B2
(45) Date of Patent: Dec. 24, 2019

(54) FACTOR VIII FORMULATIONS

(71) Applicants: BAXALTA INCORPORATED, Bannockburn, IL (US); UNIVERSITY OF CONNECTICUT, Farmington, CT (US)

(72) Inventors: Michael Pikal, Mansfield Center, CT (US); Serguei Tchessalov, Andover, MA (US); Erik Bjornson, Studio City, CA (US); Feroz Jameel, Newbury Park, CA (US); Marc Besman, Seattle, WA (US)

(*) Notice: Subject to any disclaimer, the term of this patent is extended or adjusted under 35 U.S.C. 154(b) by 0 days.

(21) Appl. No.: 15/145,131

(22) Filed: May 3, 2016

(65) Prior Publication Data

US 2017/0087218 A1  Mar. 30, 2017

Related U.S. Application Data

(63) Continuation of application No. 12/614,090, filed on Nov. 6, 2009, now abandoned.

(60) Provisional application No. 61/112,513, filed on Nov. 7, 2008.

(51) Int. Cl.
| | |
|---|---|
| A61K 38/37 | (2006.01) |
| A61K 9/00 | (2006.01) |
| A61K 9/19 | (2006.01) |
| A61K 47/02 | (2006.01) |
| A61K 47/10 | (2017.01) |
| A61K 47/18 | (2017.01) |
| A61K 47/20 | (2006.01) |
| A61K 47/26 | (2006.01) |

(52) U.S. Cl.
CPC .......... *A61K 38/37* (2013.01); *A61K 9/0019* (2013.01); *A61K 9/19* (2013.01); *A61K 47/02* (2013.01); *A61K 47/10* (2013.01); *A61K 47/18* (2013.01); *A61K 47/183* (2013.01); *A61K 47/20* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 3,770,631 | A | 11/1973 | Fekete et al. |
| 3,839,314 | A | 10/1974 | Fekete et al. |
| 3,893,990 | A | 7/1975 | Fekete et al. |
| 3,893,991 | A | 7/1975 | Fekete et al. |

(Continued)

FOREIGN PATENT DOCUMENTS

| | | |
|---|---|---|
| CA | 1 187 410 A1 | 5/1985 |
| CA | 2 065 553 C | 6/2003 |

(Continued)

OTHER PUBLICATIONS

US 5,659,014 A, 08/1997, Bhattacharya (withdrawn)

(Continued)

*Primary Examiner* — Marsha Tsay
(74) *Attorney, Agent, or Firm* — Morgan, Lewis & Bockius LLP

(57) ABSTRACT

A Factor VIII (FVIII) composition formulated such that NaCl is not present in the final formulation or is present in trace amounts, which allows for a concomitant reduction in the lyophilization cycle time and increased stability of the lyophilized FVIII.

19 Claims, 5 Drawing Sheets

(56) References Cited

U.S. PATENT DOCUMENTS

| | | |
|---|---|---|
| 3,980,432 A | 9/1976 | Trobisch |
| 4,027,013 A | 5/1977 | Bick et al. |
| 4,069,216 A | 1/1978 | Shanbrom |
| 4,073,886 A | 2/1978 | Kehn |
| 4,085,095 A | 4/1978 | Bick et al. |
| 4,086,218 A | 4/1978 | Shanbrom et al. |
| 4,089,944 A | 5/1978 | Thomas |
| 4,105,650 A | 8/1978 | Shanbrom et al. |
| 4,137,223 A | 1/1979 | Shanbrom et al. |
| 4,189,425 A | 2/1980 | Shanbrom et al. |
| 4,229,435 A | 10/1980 | Blomback et al. |
| 4,297,344 A | 10/1981 | Schwinn et al. |
| 4,327,086 A | 4/1982 | Fukushima |
| 4,341,764 A | 7/1982 | Wallace |
| 4,370,264 A | 1/1983 | Kotitschke et al. |
| 4,382,083 A | 5/1983 | Thomas |
| 4,386,068 A | 5/1983 | Mitra |
| 4,387,092 A | 6/1983 | Liautaud et al. |
| 4,404,131 A | 9/1983 | Schwarz et al. |
| 4,440,679 A | 4/1984 | Fermandes et al. |
| 4,446,134 A | 5/1984 | Naito et al. |
| 4,455,301 A | 6/1984 | Mitra et al. |
| 4,479,938 A | 10/1984 | Thomas |
| 4,481,189 A | 11/1984 | Prince |
| 4,495,175 A | 1/1985 | Chavin |
| 4,495,278 A | 1/1985 | Thomas |
| 4,522,751 A | 6/1985 | Linnau |
| 4,540,573 A | 9/1985 | Neurath et al. |
| 4,543,210 A | 9/1985 | Mitra et al. |
| 4,562,072 A | 12/1985 | Heimburger et al. |
| 4,591,505 A | 5/1986 | Prince |
| 4,613,501 A | 9/1986 | Horowitz |
| 4,623,717 A | 11/1986 | Fernandex et al. |
| 4,640,834 A | 2/1987 | Eibl et al. |
| 4,650,858 A | 3/1987 | Rasmussen |
| 4,693,981 A | 9/1987 | Wiesehahn |
| 4,727,027 A | 2/1988 | Wiesehahn et al. |
| 4,739,039 A | 4/1988 | Vasquez et al. |
| 4,743,680 A | 5/1988 | Mathews et al. |
| 4,748,120 A | 5/1988 | Wiesehahn |
| 4,757,006 A | 7/1988 | Toole, Jr. et al. |
| 4,758,657 A | 7/1988 | Farb et al. |
| 4,783,441 A | 11/1988 | Thurow |
| 4,795,806 A | 1/1989 | Brown et al. |
| 4,803,073 A | 2/1989 | Doeschel et al. |
| 4,814,435 A | 3/1989 | Schwarz |
| 4,831,012 A | 5/1989 | Estep |
| 4,841,023 A | 6/1989 | Horowitz |
| 4,847,362 A | 7/1989 | Mattews et al. |
| 4,849,508 A | 7/1989 | Magnin et al. |
| 4,876,241 A | 10/1989 | Feldman et al. |
| 4,877,608 A * | 10/1989 | Lee .............. A61K 9/0019 424/130.1 |
| 4,891,319 A | 1/1990 | Roser |
| 4,946,648 A | 8/1990 | Dichtelmuller et al. |
| 4,952,675 A | 8/1990 | Mathews et al. |
| 4,960,757 A | 10/1990 | Kumpe et al. |
| 4,981,951 A | 1/1991 | Tsay |
| 5,043,428 A | 8/1991 | Heimburger et al. |
| 5,047,249 A | 9/1991 | Rothman et al. |
| 5,051,353 A | 9/1991 | Stratton |
| 5,116,950 A | 5/1992 | Miyano et al. |
| 5,138,034 A | 8/1992 | Uemura |
| 5,177,191 A | 1/1993 | Brockway et al. |
| 5,180,583 A | 1/1993 | Hedner |
| 5,192,743 A | 3/1993 | Hsu et al. |
| 5,198,349 A | 3/1993 | Kaufman |
| 5,232,844 A | 8/1993 | Horowitz et al. |
| 5,245,014 A | 9/1993 | Kaersgaard |
| 5,250,421 A | 10/1993 | Kaufman et al. |
| 5,252,709 A | 10/1993 | Burnouf et al. |
| 5,252,710 A | 10/1993 | Dazey et al. |
| 5,254,350 A | 10/1993 | Barrow |
| 5,259,951 A | 11/1993 | Arrighi et al. |
| 5,272,135 A | 12/1993 | Takruri |
| 5,288,853 A | 2/1994 | Bhattacharva et al. |
| 5,304,638 A | 4/1994 | Marshall et al. |
| 5,328,694 A | 7/1994 | Schwinn |
| 5,356,878 A | 10/1994 | Brockway et al. |
| 5,371,195 A | 12/1994 | Grandgeorge et al. |
| 5,378,601 A | 1/1995 | Gepner-Puszkin |
| 5,378,612 A | 1/1995 | Nakashima et al. |
| 5,399,670 A | 3/1995 | Bhattacharya et al. |
| 5,408,039 A | 4/1995 | Burnouf-Radosevich |
| 5,410,022 A | 4/1995 | Eibl et al. |
| 5,418,130 A | 5/1995 | Platz et al. |
| 5,424,401 A | 6/1995 | Heimburger et al. |
| 5,439,882 A | 8/1995 | Feola |
| 5,514,781 A | 5/1996 | Dobkin |
| 5,565,427 A | 10/1996 | Freudenberg |
| 5,580,856 A | 12/1996 | Prestrelski et al. |
| 5,587,490 A | 12/1996 | Goodrich, Jr. |
| 5,605,884 A | 2/1997 | Lee et al. |
| 5,679,549 A | 10/1997 | Chan |
| 5,679,776 A | 10/1997 | Burnouf-Radosevich |
| 5,693,499 A | 12/1997 | Yonemura et al. |
| 5,712,086 A | 1/1998 | Horowitz et al. |
| 5,733,873 A | 3/1998 | Osterberg et al. |
| 5,760,183 A | 6/1998 | Dazey et al. |
| 5,763,401 A | 6/1998 | Nayar |
| 5,780,295 A | 7/1998 | Livesey |
| 5,798,238 A | 8/1998 | Goodrich, Jr. |
| 5,851,800 A | 12/1998 | Adamson |
| 5,858,375 A | 1/1999 | Furminger |
| 5,874,408 A | 2/1999 | Nayar |
| 5,919,443 A | 7/1999 | Michaelis et al. |
| 5,919,766 A | 7/1999 | Osterberg et al. |
| 5,919,908 A | 7/1999 | Osterberg et al. |
| 5,955,448 A | 9/1999 | Colaco |
| 6,005,082 A | 12/1999 | Smeds |
| 6,440,414 B1 | 8/2002 | Kendrick et al. |
| 6,586,573 B1 | 7/2003 | Besman et al. |
| 6,649,386 B2 | 11/2003 | Roser |
| 7,087,723 B2 | 8/2006 | Besman et al. |
| 7,247,707 B2 | 7/2007 | Besman et al. |
| 7,790,680 B2 | 9/2010 | White et al. |
| 8,058,226 B2 | 11/2011 | Besman et al. |
| 2009/0291076 A1 | 11/2009 | Morichika et al. |

FOREIGN PATENT DOCUMENTS

| | | |
|---|---|---|
| CN | 1047342 A | 11/1990 |
| CN | 1181974 A | 5/1998 |
| DE | 3904354 A1 | 8/1990 |
| DE | 4431833 C1 | 5/1995 |
| EP | 0 117 064 A2 | 8/1984 |
| EP | 0 123 945 A1 | 11/1984 |
| EP | 0 127 025 A2 | 12/1984 |
| EP | 0 131 740 A2 | 1/1985 |
| EP | 0 137 428 A2 | 4/1985 |
| EP | 0 171 506 A1 | 2/1986 |
| EP | 0 209 041 A2 | 1/1987 |
| EP | 0 237 981 A2 | 9/1987 |
| EP | 0 306 968 | 3/1989 |
| EP | 0 314 095 | 5/1989 |
| EP | 0 315 968 | 5/1989 |
| EP | 0 077 870 B1 | 7/1989 |
| EP | 0 212 040 B1 | 5/1990 |
| EP | 0 399 321 A2 | 11/1990 |
| EP | 0 410 207 A2 | 1/1991 |
| EP | 0 035 204 | 5/1991 |
| EP | 0 229 810 B | 10/1991 |
| EP | 0 468 181 A2 | 1/1992 |
| EP | 0 150 735 B1 | 7/1992 |
| EP | 0 508 194 | 10/1992 |
| EP | 0 292 003 B1 | 3/1994 |
| EP | 0 600 480 A2 | 6/1994 |
| EP | 0 383 234 B1 | 11/1994 |
| EP | 0 771 567 A1 | 5/1997 |
| EP | 0 818 204 | 1/1998 |
| GB | 941019 A | 4/1961 |
| GB | 2085729 A | 5/1982 |
| GB | 2129685 A | 5/1984 |
| JP | 56-127308 A | 10/1981 |

(56) References Cited

FOREIGN PATENT DOCUMENTS

| | | | |
|---|---|---|---|
| JP | 60-199829 A | 10/1985 | |
| JP | 61-022022 A | 1/1986 | |
| JP | 61-271222 A | 12/1986 | |
| JP | 62-195331 A | 8/1987 | |
| JP | 64-075431 A | 3/1989 | |
| JP | 01-149733 A | 6/1989 | |
| JP | 01-157917 A | 6/1989 | |
| JP | 02-157231 A | 6/1990 | |
| JP | 05-331071 A | 12/1993 | |
| JP | 07-501560 A | 2/1995 | |
| JP | 08-053361 A | 2/1996 | |
| JP | 08-504784 A | 5/1996 | |
| JP | 08-509745 A | 10/1996 | |
| JP | 09-025241 A | 1/1997 | |
| JP | 10-067679 A | 3/1998 | |
| SE | 468480 B | 1/1993 | |
| SU | 663404 A1 | 5/1979 | |
| WO | WO 89/06547 A1 | 7/1989 | |
| WO | WO 89/09784 A1 | 10/1989 | |
| WO | WO 91/18017 A1 | 11/1991 | |
| WO | WO 92/01229 A1 | 1/1992 | |
| WO | WO 93/00807 A1 | 1/1993 | |
| WO | WO 93/10143 A1 | 5/1993 | |
| WO | WO 93/22336 A1 | 11/1993 | |
| WO | WO 93/22337 A1 | 11/1993 | |
| WO | WO 94/03179 A1 | 2/1994 | |
| WO | WO 1994/07510 A1 | 4/1994 | |
| WO | WO 94/17834 A1 | 8/1994 | |
| WO | WO 94/26286 A1 | 11/1994 | |
| WO | WO 95/01804 A1 | 1/1995 | |
| WO | WO 95/07713 A1 | 3/1995 | |
| WO | WO 95/26750 A1 | 10/1995 | |
| WO | WO 95/33488 A1 | 12/1995 | |
| WO | WO 96/05809 A1 | 2/1996 | |
| WO | WO 96/15150 A1 | 5/1996 | |
| WO | WO 96/19918 A1 | 7/1996 | |
| WO | WO 1996/022107 A1 | 7/1996 | |
| WO | WO 96/30041 A1 | 10/1996 | |
| WO | WO 97/11957 A1 | 4/1997 | |
| WO | WO 97/16966 A1 | 5/1997 | |
| WO | WO 97/19687 A1 | 6/1997 | |
| WO | WO 97/42980 A1 | 11/1997 | |
| WO | WO 2000/048635 | 8/2000 | |
| WO | WO-0048635 A1 * | 8/2000 | ........... A61K 9/0019 |
| WO | WO 2001/003726 | 1/2001 | |
| WO | WO 2004/039337 | 5/2004 | |
| WO | WO 2005/058283 A2 | 6/2005 | |
| WO | WO 2007/124090 A2 | 11/2007 | |
| WO | WO 2010/026186 A1 | 3/2010 | |

OTHER PUBLICATIONS

Carpenter, J.F., et al. 2002 Rational Design of Stable Protein Formulations, Pharmaceutical Biotechnology vol. 13: 109-133. (Year: 2002).*

Adbul-Fattah et al., The effect of annealing on the stability of amorphous solids: Chemical stability of freeze-dried moxalactam. *J. Pharm. Sci.* 96: 1237-50 (2007).

Andersson et al., Isolation and characterization of human factor VIII: molecular forms in commercial factor VIII concentrate, cryoprecipitate, and plasma, *Proc. Natl. Acad. Sci. USA.* 83: 2979-83 (1986).

Arakawa et al., Preferential interactions of proteins with solvent components in aqueous amino acid solutions, *Arch. Biochem. Biophys.* 224: 169-77 (1983).

Arakawa et al., Protein-solvent interactions in pharmaceutical formulations, *Pharm. Res.* 8: 285-91 (1991).

Arakawa et al., The stabilization of beta-lactoglobulin by glycine and NaCl. *Biopolymers*, 28: 1397-401 (1989).

Austen et al., Factor VIII fractionation on aminohezyl sepharose with possible reduction in hepatitis B antigen, *Throm. Haemostas.*, 48(1): 46-8 (1982).

Austen, The chromatographic separation of factor VIII on aminohexyl sepharose, *Brit. J. Haematol.*, 43: 669-74 (1979).

Ben-Hur et al., Virus inactivation in red cell concentrates by photosensitization with phthalocyanines: Protection of red cells but not of vesicular stomatitis virus with a water soluble analogue of vitamin E, *Transfusion*, 35: 401-6 (1995).

Bhatnagar et al., Study of the individual contributions of ice formation and freeze-concentration on isothermal stability of lactate dehydrogenase during freezing. *J. Pharm Sci.* 97(2): 798-814 (2008).

Blolmback et al., The effect of reducing agents on factor VIII and other coagulation factors, *Thromb. Res.*, 12: 1177-94 (1978).

Bohnert et al., Changes in adsorbed fibrinogen and albumin interactions with polymers indicated by decreases in detergent elutability, *J. Colloid Interface Sci.*, 3(2): 363-77 (1986).

Burnouf et al., A highly purified factor VIII:c concentrate prepared from cryoprecipitate by ion-exchange chromatography, *Vox Sang.*, 60: 8-15 (1991).

Carpenter et al., Interactions of stabilizing additives with proteins during freeze-thawing and freeze-drying, *Dev. Biol. Stand.* 74: 225-39 (1991).

Carpenter et al., Lyophilization of Protein Pharmaceuticals, Chapter 4 in *Biotechnology and Biopharmaceutical Manufacturing, Processing, and Preservation*, Avis, K.E. et al., eds., Interpharm Press Inc., Buffalo Grove, IL, pp. 199-264 (1996).

Carpenter et al., Rational design of stable lyophilizes protein formulations: Some practical advice, *Pharm. Res.* 14: 969-75 (1997).

Carpenter et al., Separation of freezing- and drying-induced denaturation of lyophilized proteisn by stress-specific stabilization: Enzyme activity and calorimetric-studies, *Arch. Biochem. Biophys.* 303: 456-64 (1993).

Carpenter, J.F. et al., "Rational Design of Stable Protein Formulations," *Pharmaceutical Biotechnology*, 2002, vol. 13:109-133.

Chang et al., Development of a stable free-dried formulation of recombinant human interleukin-1 receptor antagonist. *Pharm Res.* 13:243-9 (1996).

Chang et al., Development of a stable freeze-dried formulation of recombinant human interleukin-1 receptor antagonist, *Pharma. Res.*, 13(2): 243-9 (1996).

Chang et al., Development of an efficient single-step freeze-drying cycle for protein formulations, *Pharma. Res.*, 12(6): 831-7 (1995).

Chang et al., Surface-induced denaturation of proteins during freezing and its inhibition by surfactants. *J. Pharm. Sci.* 85:1325-30 (1996).

Chang et al., Use of subambient thermal analysis to optimize protein lyophilization, *Cryobiology*, 29: 632-56 (1992).

Chen et al., Influence of calcium ions on the structure and stability of recombinant human deoxyribonuclease I in the aqueous and lyophilized states. *J Pharm Sci.* 88(4): 477-82 (1999).

Chen et al., Influence of histidine on the stability and physical properties of a fully human antibody in aqueous and solid forms. *Pharm Res.*, 20(12): 1952-60 (2003).

Chen et al., Protection of vitamin E, selenium, Trolox C, ascorbic acid, palmitate, acetylcysteine, coenzyme Q0, coenzyme Q10, beta-carotene, canthazanthin, and (+)-catechin against oxidative damage to rat blood and tissues in vivo, *Free Radical Biology & Medicine*; 18: 949-53 (1995).

Chen, Formulation concerns of protein drugs. *Drug Dev. Indust. Pharm.* 18(11&12):1311-54 (1992).

Chin et al., Virucidal short wavelength ultraviolet light treatment of plasma and factor VIII concentrate: Protection of proteins by antioxidants, *Blood*, 86(11): 4331-6 (1986).

Cleland et al. (Eds.), Formulation and delivery of protein and peptides, Chapter 1 (Jeffrey L. Cleland) and Chapter 8 (Michael J. Pikal), pp. 1-17 & 120-133 (1994).

Derrick et al., Effect of metal cations on the conformation and inactivation of recombinant human factor VIII. *J. Pharm. Sci.*, 93(10): 2549-57 (2004).

Dwight et al., The effects of tert-butyl hydroperoxideon human erythrocyte membrane ion transport and the protective actions of antioxidants, *Clinica Chimica Acta*, 249: 167-81 (1996).

Edwards et al., Tri (n-butyl) phosphate/detergent treatment of licensed therapeutic and experimental blood derivatives, *Vox Sang.*, 52: 53-9 (1987).

(56) References Cited

OTHER PUBLICATIONS

Fatouros et al., Recombinant factor VIII SQ—influence of oxygen, metal ions, pH and ionic strength on its stability in aqueous solution. *Int. J. Pharm.*, 155: 121-31 (1997).
Fatouros et al., Recombinant factor VIII SQ: Stability in solution; Sixteenth ISTH meeting, Florence, Jun. 6-12, 1997.
Fatouros et al., Recombinant factor VIII SQ-inactivation kinetics in aqueous solution and the influence of disaccharides and sugar alcohols, *Pharma. Res.*, 14(12): 1679-84 (1997).
Fatouros, Pharmaceutical formulations and impact on protein structure and stability, Recombinant Factor VIII SQ, The Royal Danish School of Pharmacy, Department of Pharmaceutics, Copenhagen and bibliographic index data indicating publication year (1998).
Faure et al., Improved buffer for the chromatographic separation of factor VIII coagulant, *J. Chromatogr.*, 391(257): 398-1 (1983).
Foster et al., Studies on the stability of VIII:C during the manufacture of a factor VIII concentrate for clinical use, *Vox Sang*, 55: 81-9 (1988).
Franks et al., Long-term stabilization of biologicals. *Biotechnology (N.Y.)*, 12: 253-6 (1994).
Gekko et al., Induced thermal stability of collagen in the presence of sugars and polyols. *J. Biochem.* 94: 199-205 (1983).
Gekko et al., Polyol-induced stabilization of a cold-labile protein, *Argic Biol. Chem.* 55: 1663-4 (1991).
Gitschier et al., Characterization of the human Factor VIII gene, *Nature*, 312(5992): 326-30 (1984).
Goulian et al., Stabilization of factor 8 by glycerol, *Nature*, 211(44): 74-5 (1966).
Hart et al., Effect of terminal (dry) heat treatment on non-enveloped viruses in coagulation factor concentrates, *Vox Sang.*, 67: 345-50 (1994).
Hawe, A., et al., *European Journal of Pharmaceutical Sciences*, 2006, vol. 28:224.232.
Heimberger et al., Faktor VIII-Konzentrat hochgereinigt and in Losung erhitzt, Drug Res., 31: 619 (1981).
Heller et al., Manipulation of lyophilization-induced phase separation: implications for pharmaceutical proteins, *Biotechnol. Prog.*, 13(5): 590-6 (1991).
Her et al., Electrolyte-induced changes in glass transition temperatures of freeze-concentrated solutes, *Pharm. Res.* 12 (1995).
Hollander-Rodriguez et al., Hyperkalemia. *Am. Fam. Physician.*, 73(2): 283-90 (2006).
Horowitz et al., Inactivation of lipid-enveloped viruses in labile blood derivatives. II. Physical methods, *Vox Sang.*, 54: 14-20 (1988).
Horowitz et al., Inactivation of viruses in labile blood derivatives. II. Physical methods, *Transfusion*, 25: 523-7 (1985) (Abstract only from Index Medicurs, Medline database).
International Search Report, PCT/US2009/063610, European Patent Office, dated Jan. 26, 2010.
Jameel et al., Development of freeze-dried biosynthetic factor VIII: I. A case study in the of optimization of formulation, *Pharm. Dev. Tech.* (2009).
Kappelgaard, Liquid growth hormone: Preservation and buffers. *Horm Res.* 62 Suppl 3:98-103 (2004).
Kowolenko et al., Preclinical evaluation of an improved formulation of human recombinant FVIII (Kogenate-2): toxicology, pharmacology, pharmacokinetics, and neoantigenicity, *Thromb. & Haemostatis Suppl.*, Abstract No. PS-2084: 509 (1993).
Lam et al., Antioxidants for prevention of methionine oxidation in recombinant monoclonal antibody HER2. *J. Pharm. Sci.* 86(11): 1250-5 (1997).
Laursen et al., Pain perception after subcutaneous injections of media containing different buffers. *Basic Clin Pharmacol Toxicol.*, 98(2): 218-21 (2006).
Lee et al., The stabilization of proteins by sucrose, *J. Biol.Chem.* 256: 7193-202 (1981).
Lueckel et al., Formulations of sugars with amino acids or mannitol-influence of concentration ratio on the properties of the freeze-concentrate and the lyophilizate, *Pharma. Dev. Technol.*, 3(3): 325-36 (1998).
Mackenzie, Non-equilibrium freezing behaviour of aqueous systems [and discussion]. *Phil. Trans. R. Soc. Lond.* 278:167-89 (1977).
Manning et al., Stability of protein pharmaceuticals, *Pharma. Res.*, 6(11): 903-18 (1989).
Margolis-Nunno et al., Virus sterilization in platelet concentrates with psoralen and ultraviolet A light in the presence of quenchers, *Transfusion*, 32: 541-7 (1992).
McIntosh et al., A high-yield factor VIII concentrate suitable for advanced heat treatment, *Thromb. Haemost.*, Abstract No. 1119: 309 (1987).
McIntosh et al., The effect of solution formulation on the stability and surface interactions of factor VIII during plasma fractionation, *Transfus. Sci.*; 11: 55-66 (1990).
Minogue et al., Bacteriostatic saline containing benzyl alcohol decreases the pain associated with the injection of propofol. *Anesth Analg.*, 100(3): 683-6 (2005).
Morganthaler, Chromatography of antihemophilic factor on diaminoalkane- and aminoalkane-derivatized sepharose, Throm. Haemost., 47(2): 124-7 (1992).
Nayar et al., Recombinate Kogenate®, formulation development, *Thromb. & Haemostasis Suppl.*, Abstract No. PS-2081: 509 (1993).
Oguchi et al., Freeze-drying of drug-additive binary systems III. Crystallization of α-cyclodextrin inclusion complex in freezing process, *Int. J. Pharmac.*, 61: 27-34 (1990).
Osterberg et al., Development of a freeze-dried albumin-free formulation of recombinant factor VIII SQ, *Pharm. Res.* 14: 892-8 (1997).
Osterberg et al., Development of a freezer-dried HAS-free formulation of a new recombinant factor VIII derivative, r-VIII SQ, ISTH Poster Abstract Book; p. 1099—Abstract 1984 (1993).
Over et al., Methodology of the one-stage assay of factor VIII, *Scand. J. Haematol.* 33:(suppl. 41): 12-24 (1984).
Owen et al., Antihemophilic factor: Separation of an active fragment following dissociation by salts or detergents, *Thrombosis et Diathesis Haemorrhagica*, XXVII(3): 502-15 (1972).
Palmer et al., Development of a heat-treated factor VIII/von Williebrand factor concentrate prepared from heparinized plasma, *Thromb. Haemost.*, 63(3): 392-402 (1990).
Parti et al., In vitro stability of recombinant human factor VIII (recombinate TM). *Haemophilia*, 6: 513-22 (2000).
Pikal et al., Development of freeze-dried biosynthetic factor VIII: II. A case study in process optimization, *Pharm. Dev. Technol.* 14(6): 687-97 (2009).
Pikal et al., Solid state chemistry of proteins: II. The correlation of storage stability of freeze-dried human growth hormone (hGH) with structure and dynamics in the glassy solid, *J. Pharm. Sci.* 97(12): 5106-21 (2008).
Pikal et al., The stability of insulin in crystalline and amorphous solids: Observations of greater stability for the amorphous form. *Pharm. Res.* 14: 1379-87 (1997).
Potera, A sweet way to keep proteins safe, *Science*, 281(5384): 1973 (1998).
Powell et al., Compendium of Excipients fir Parenteral Formulations. *PDA J. Pharm. Sci. Technol.* 52:238-311 (1998).
Remmele et al., Interleukin-1 receptor (IL-1R) liquid formulations development using differential scanning calorimetry. *J. Pharm Res.*, 15(2): 200-8 (1998).
Remmele et al., Minimization of recombinant human Flt2 ligand aggregation at the Tm plateau: A matter of thermal reversibility. *Biochemistry*, 38(16): 5241-7 (1999).
Ronzi et al., Optimisation of a freeze-drying process of high purity factor VIII and factor IX concentrates, *Chem. Eng. Processing*, 42: 751-7 (2003).
Roser, Trehalose drying: A novel replacement for freeze-drying, *Biopharm.*, 4(8): 47-53 (1991).
Roy et al., Effects of benzyl alcohol on aggregation of recombinant human interleukin-1-receptor antagonist in reconstituted lyophilized formulations. *J Pharm Sci.*, 94(2): 382-96 (2005).

(56) References Cited

OTHER PUBLICATIONS

Rywkin et al., Importance of type I and type II mechanisms in the photodynamic inactivation of viruses in blood with aluminum phthalocyanine derivatives, *Photochem. Photobiol.*, 56: 463-9 (1992).

Sugiyama et al., Purpurgallin as an antioxidant protector of human erythrocytes against lysis by peroxyl radicals, *Life Sci.*, 53: 39-43 (1993).

Tandon et al., Detergent-assisted refolding of guanidinium chloride-denatured rhodanese, *J. Biol. Chem.*, 262(10): 4486-91 (1987).

Tang et al., Design of freeze-drying processes for pharmaceuticals: Practical advice. *J. Pharm Res.* 21:191-200, (2004).

Thompson, Structure and function of the factor VIII gene and protein, *Semin Thromb Hemost*, 29:11-29 (2002).

Tomita et al., Sensitized photooxidation of histidine and its derivatives. Products and mechanism of the reaction. *Biochemistry*, 8(12): 5149-60 (1969).

UniProtKB/Swiss-Prot Accession No. P00451 (FA8_HUMAN), dated Mar. 2, 2010.

Vehar et al., Structure of human Factor VIII, Nature, 312(5992):337-42 (1984).

Wang et al., Effect of collapse on the stability of freeze-dried recombinant factor VIII and ALPHA-amylase, *J. Pharm. Sci.* 93: 1253-63 (2004).

Yin et al., Effects of antioxidants on the hydrogen peroxide-mediated oxidation of methionine residues in granulocyte colony-stimulating factor and human parathyroid hormone fragment 13-34. *J. Pharm Res.* 21(12): 2377-83 (2004).

Yoshioka et al., Usefulness of the Kohirausch Williams-Watts stretched exponential function to describe protein aggregation in lyophilized formulations and the temperature dependence near glass transition temperature, *Pharm. Res.* 18: 256-60 (2001).

Yu et al., Existence of a mannitol hydrate during freeze-drying and practical implications, *J. Pharm. Sci.* 88: 196-8 (1999).

\* cited by examiner

● = 25°C; ■ = 40°C; ▲ = 50°C

A.

B.

Key: open bars = 50°C, shaded bars = 40°C, solid bars = 25°C. Error bars represent standard errors as given by the regression analysis. In general, maximum storage times were 3 months (50°C), 6 months (40°), and 12 months (25°).

FACTOR VIII FORMULATIONS

FIELD OF THE INVENTION

Generally, the invention relates to a Factor VIII composition formulated such that NaCl is not present in the final formulation or is present in trace amounts, which allows for a concomitant reduction in the lyophilization cycle time and increased stability of the lyophilized Factor VIII.

BACKGROUND OF THE INVENTION

Factor VIII (FVIII) is a protein found in blood plasma, which acts as a cofactor in the cascade of reactions leading to blood coagulation. A deficiency in the amount of FVIII activity in the blood results in the clotting disorder known as hemophilia A, an inherited condition primarily affecting males. Hemophilia A is currently treated with therapeutic preparations of FVIII derived from human plasma or manufactured using recombinant DNA technology. Such preparations are administered either in response to a bleeding episode (on-demand therapy) or at frequent, regular intervals to prevent uncontrolled bleeding (prophylaxis).

FVIII is known to be relatively unstable in therapeutic preparations. In blood plasma, FVIII is usually complexed with another plasma protein, von Willebrand factor (vWF), which is present in plasma in a large molar excess to FVIII and is believed to protect FVIII from premature degradation. Another circulating plasma protein, albumin, may also play a role in stabilizing FVIII in vivo. Currently marketed FVIII preparations therefore primarily rely on the use of albumin and/or vWF to stabilize FVIII during the manufacturing process and during storage.

The albumin and vWF used in currently marketed FVIII preparations are derived from human blood plasma, however, and the use of such material has certain drawbacks. Because a large molar excess of albumin compared to FVIII is generally added in order to increase the stability of the FVIII in such preparations, it is difficult to characterize the FVIII protein itself in these preparations. The addition of human-derived albumin to FVIII is also perceived as being a disadvantage with respect to recombinantly-produced FVIII preparations. This is because, in the absence of such added albumin, the theoretical risk of transmitting a virus would be reduced in recombinantly-derived FVIII preparations.

Several attempts to formulate FVIII without albumin or vWF (or with relatively low levels of these excipients) have been described. For example, U.S. Pat. No. 5,565,427 (EP 508 194) to Freudenberg (assigned to Behringwerke) describes FVIII preparations which contain particular combinations of detergent and amino acids, specifically arginine and glycine, in addition to excipients such as sodium chloride and sucrose. The detergent, polysorbate 20 or polysorbate 80, is described as being present in amounts of between 0.001 to 0.5% (v/v), while arginine and glycine are present in amounts of between 0.01 to 1 mol/l. Sucrose is described as being present in amounts of between 0.1 and 10%. Example 2 of this patent alleges that solutions of (1) 0.75% sucrose, 0.4 M glycine, and 0.15M NaCl, and (2) 0.01 M sodium citrate, 0.08 M glycine, 0.016M lysine, 0.0025 M calcium chloride, and 0.4 M sodium chloride were not stable in solution over 16 hours, whereas solutions of (3) 1% sucrose, 0.14 M arginine, 0.1 M sodium chloride and (4) 1% sucrose, 0.4 M glycine, 0.14 M arginine, 0.1 M sodium chloride, and 0.05% TWEEN™. 80 (polysorbate 80) exhibited stability.

U.S. Pat. No. 5,763,401 (EP 818 204) to Nayer (assigned to Bayer) also describes a therapeutic FVIII formulation without albumin, comprising 15-60 mM sucrose, up to 50 mM NaCl, up to 5 mM calcium chloride, 65-400 mM glycine, and up to 50 mM histidine. The following specific formulations were identified as allegedly being stable: (1) 150 mM NaCl, 2.5 mM calcium chloride, and 165 mM mannitol; and (2) 1% sucrose, 30 mM sodium chloride, 2.5 mM calcium chloride, 20 mM histidine, and 290 mM glycine. A formulation containing higher amounts of sugar (10% maltose, 50 mM NaCl, 2.5 mM calcium chloride, and 5 mM histidine) was allegedly found to exhibit poor stability in the lyophilized state compared with formulation (2).

U.S. Pat. No. 5,733,873 (EP 627 924) to Osterberg (assigned to Pharmacia & Upjohn) discloses formulations which include between 0.01-1 mg/ml of a surfactant. This patent discloses formulations having the following ranges of excipients: polysorbate 20 or 80 in an amount of at least 0.01 mg/ml, preferably 0.02-1.0 mg/ml; at least 0.1 M NaCl; at least 0.5 mM calcium salt; and at least 1 mM histidine. More particularly, the following specific formulations are disclosed: (1) 14.7, 50, and 65 mM histidine, 0.31 and 0.6 M NaCl, 4 mM calcium chloride, 0.001, 0.02, and 0.025% polysorbate 80, with or without 0.1% PEG 4000 or 19.9 mM sucrose; and (2) 20 mg/ml mannitol, 2.67 mg/ml histidine, 18 mg/ml NaCl, 3.7 mM calcium chloride, and 0.23 mg/ml polysorbate 80.

Other attempts to use low or high concentrations of sodium chloride have also been described. U.S. Pat. No. 4,877,608 (EP 315 968) to Lee (assigned to Rhone-Poulenc Rorer) discloses formulations with relatively low concentrations of sodium chloride, namely formulations comprising 0.5 mM to 15 mM NaCl, 5 mM calcium chloride, 0.2 mM to 5 mM histidine, 0.01 to 10 mM lysine hydrochloride and up to 10% sugar. The "sugar" can be up to 10% maltose, 10% sucrose, or 5% mannitol.

U.S. Pat. No. 5,605,884 (EP 0 314 095) to Lee (assigned to Rhone-Poulenc Rorer) teaches the use of formulations with relatively high concentrations of sodium chloride. These formulations include 0.35 M to 1.2 M NaCl, 1.5 to 40 mM calcium chloride, 1 mM to 50 mM histidine, and up to 10% of a "sugar" such as mannitol, sucrose, or maltose. A formulation comprising 0.45 M NaCl, 2.3 mM calcium chloride, and 1.4 mM histidine is exemplified.

International Patent Application WO 96/22107 to Roser (assigned to Quadrant Holdings Cambridge Limited) describes formulations which include the sugar trehalose. These formulations comprise: (1) 0.1 M NaCl, 15 mM calcium chloride, 15 mM histidinetr, and 1.27 M (48%) ehalose; or (2) 0.011% calcium chloride, 0.12% histidine, 0.002% Tris, 0.002% TWEEN™. 80, 0.004% PEG 3350, 7.5% trehalose, and either 0.13% or 1.03% NaCl.

U.S. Pat. No. 5,328,694 (EP 511 234) to Schwinn (assigned to Octapharma AG) describes a formulation which includes 100 to 650 mM disaccharide and 100 mM-1.0 M amino acid. Specifically, the following formulations are disclosed: (1) 0.9 M sucrose, 0.25 M glycine, 0.25 M lysine, and 3 mM calcium chloride; and (2) 0.7 M sucrose, 0.5 M glycine, and 5 mM calcium chloride.

Other therapeutic FVIII formulations of the prior art generally include albumin and/or vWF for the purpose of stabilizing FVIII and are therefore not relevant to the present disclosure. Although there exists an extensive literature focused on formulation and process development issues with freeze dried products, studies of freeze dried FVIII are limited to a study of formulations based upon use of NaCl as a bulking agent A major complication in formulation development is the presence of sodium chloride in the bulk drug substance, which is generally introduced by the purification process. As a result of the purification process, large and/or variable amounts of sodium chloride are present in the bulk drug substance solution. Uncrystallized sodium chloride lowers the collapse temperature and may leave the product incapable of being manufactured in anything resembling an elegant product. Further, the amorphous sodium chloride may compromise stability of the product. The present disclosure involves formulations for freeze drying wherein NaCl is removed or present in trace amounts, which are capable of keeping FVIII stably stored for extended periods of time.

SUMMARY OF THE INVENTION

FVIII compositions of the present disclosure are, in one embodiment, formulated such that NaCl is not present in the final formulation or is present in trace amounts, which allows for a concomitant reduction in the lyophilization cycle time and increased stability of the lyophilized FVIII.

In one embodiment, a stable lyophilized pharmaceutical formulation of FVIII is provided comprising: (a) a FVIII; (b) one or more buffering agents; (c) one or more antioxidants; (d) one or more stabilizing agents; and (e) one or more surfactants; the FVIII comprising a polypeptide selected from the group consisting of: a) a recombinant FVIII polypeptide; b) a biologically active analog, fragment or variant of a); the buffer is comprising of a pH buffering agent in a range of about 0.1 mM to about 500 mM and the pH is in a range of about 2.0 to about 12.0; the antioxidant is at a concentration of about 0.005 to about 1.0 mg/ml; the stabilizing agent is at a concentration of about 0.005 to about 20%; the surfactant is at a concentration of about 0.001% to about 1.0%; said formulation excluding sodium chloride (NaCl) or including only trace amount of NaCl.

In another embodiment, an aforementioned formulation is provided wherein the buffering agent is selected from the group consisting of citrate, glycine, histidine, HEPES, Tris and combinations of these agents. In one embodiment, the buffering agent is histidine.

In another embodiment, an aforementioned formulation is provided wherein the pH is in the range of about 6.0 to about 8.0 or about 6.5 to about 7.5. In still another embodiment, the buffering agent is histidine and the pH is about 7.0.

In one embodiment, an aforementioned formulation is provided wherein the antioxidant is glutathione. In yet another embodiment, the antioxidant is at a concentration range of about 0.1 to about 0.5 mg/ml. In still another embodiment, the antioxidant is glutathione at a concentration of about 0.2 mg/ml. In still another embodiment, the buffering agent is histidine and the pH is about 7.0; and wherein the antioxidant is glutathione at a concentration of about 0.2 mg/ml.

In another embodiment, an aforementioned formulation is provided wherein the one or more stabilizing agents is selected from the group consisting of sucrose, trehalose, and raffinose, and combinations of these stabilizing agents. In one embodiment, the stabilizing agents are trehalose at a concentration of about 5% and calcium chloride at a concentration of about 4 mM. In yet another embodiment, the stabilizing agents are sucrose at a concentration of about 5% and calcium chloride at a concentration of about 4 mM.

In one embodiment, an aforementioned formulation is provided wherein the surfactant is selected from the group consisting of digitonin, Triton X-100, Triton X-114, TWEEN-20, TWEEN-80 and combinations of these surfactants. In still another embodiment, the surfactant is TWEEN-80 at about 0.03%.

In one embodiment, an aforementioned formulation is provided wherein the buffering agent is histidine at a concentration of about 25 mM at about pH 7.0; wherein the antioxidant is glutathione at a concentration of about 0.2 mg/ml; wherein the stabilizing agents are trehalose or sucrose at a concentration of about 5% and calcium chloride at a concentration of about 4 mM.; and wherein the surfactant is TWEEN-80 at about 0.03%.

In yet another embodiment, an aforementioned formulation is provided wherein NaCl is not added as an excipient. In still another embodiment, NaCl is present in trace amount following removal by dialysis or solvent exchange chromatography.

Methods of preparing a stable, lyophilized FVIII are provided in the present disclosure. In one embodiment, a method of preparing a stable, lyophilized FVIII is provided comprising the steps of (a) preparing an aforementioned formulation; and (b) lyophilizing the formulation of step (a). In still another embodiment, the aforementioned method is provided wherein stability of the lyophilized FVIII is higher compared to a FVIII formulation that is lyophilized in the presence of sodium chloride.

In another embodiment, a stable lyophilized pharmaceutical formulation of FVIII is provided comprising: (a) a FVIII; (b) one or more buffering agents; (c) one or more antioxidants; (d) one or more stabilizing agents; and (e) one or more surfactants; the FVIII comprising a polypeptide selected from the group consisting of: a) a recombinant FVIII polypeptide; b) a biologically active analog, fragment or variant of a); the buffer is comprising of a pH buffering agent in a range of about 0.1 mM to about 500 mM and the pH is in a range of about 2.0 to about 12.0; the antioxidant is at a concentration of about 0.005 to about 1.0 mg/ml; the stabilizing agent is at a concentration of about 0.005 to about 20%; and the surfactant is at a concentration of about 0.001% to about 1.0%.

DETAILED DESCRIPTION OF THE INVENTION

Definitions

Figure 1:
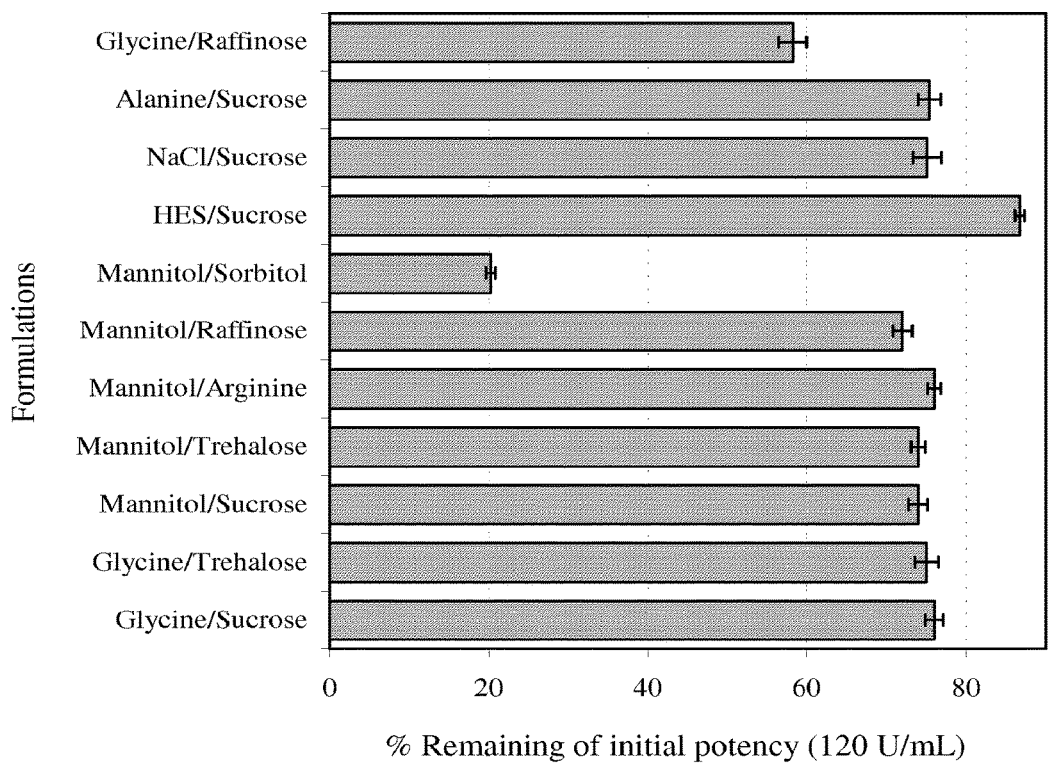
FIG. 1. Loss of FVIII during formulation and freeze-drying. Error bars are standard error calculated from replicate determinations FIG. 2. Storage stability of freeze-dried rAHF in mannitol/trehalose (FIG. 2A) and glycine/trehalose (FIG. 2B) based formulations and square root of time kinetics.

As used herein, the terms below and variations thereof shall be defined as follows, unless otherwise indicated:

Unless otherwise defined, all technical and scientific terms used herein have the same meaning as commonly understood by one of ordinary skill in the art to which this invention belongs. The following references provide one of skill with a general definition of many of the terms used in this disclosure: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that, as used in this specification and the appended claims, the singular forms "a," "an," and "the" include plural reference unless the context clearly dictates otherwise.

As used herein, the following terms have the meanings ascribed to them unless specified otherwise.

The term "comprising," with respect to a peptide compound, means that a compound may include additional amino acids at either or both amino and carboxy termini of the given sequence. Of course, these additional amino acids should not significantly interfere with the activity of the compound. With respect to a composition of the instant disclosure, the term "comprising" means that a composition may include additional components. These additional components should not significantly interfere with the activity of the composition. "Comprising" as it relates to a FVIII formulations excludes sodium chloride (NaCl) altogether, or includes NaCl in only trace amounts.

The term "pharmacologically active" means that a substance so described is determined to have activity that affects a medical parameter or disease state.

As used herein the terms "express," "expressing" and "expression" mean allowing or causing the information in a gene or DNA sequence to become manifest, for example, producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed." An expression product can be characterized as intracellular, extracellular or secreted. The term "intracellular" means inside a cell. The term "extracellular" means outside a cell, such as a transmembrane protein. A substance is "secreted" by a cell if it appears in significant measure outside the cell, from somewhere on or inside the cell.

As used herein a "polypeptide" refers to a polymer composed of amino acid residues, structural variants, related naturally-occurring structural variants, and synthetic non-naturally occurring analogs thereof linked via peptide bonds. Synthetic polypeptides are prepared, for example, using an automated polypeptide synthesizer. The term "protein" typically refers to large polypeptides. The term "peptide" typically refers to short polypeptides.

As used herein a "fragment" of a polypeptide is meant to refer to any portion of a polypeptide or protein smaller than the full-length polypeptide or protein expression product.

As used herein an "analog" refers to any of two or more polypeptides substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it.

As used herein a "variant" refers to a polypeptide, protein or analog thereof that is modified to comprise additional chemical moieties not normally a part of the molecule. Such moieties may modulate the molecule's solubility, absorption, biological half-life, etc. The moieties may alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art. For example and without limitation, in one aspect the variant is a blood clotting factor having a chemical modification which confers a longer half-life in vivo to the protein. In various aspects, polypeptides are modified by glycosylation, pegylation, and/or polysialylation.

FVIII

Herein, the term "Factor VIII" or "FVIII" or "rAHF" refers to any FVIII molecule which has at least a portion of the B domain intact, and which exhibits biological activity that is associated with native FVIII. In one embodiment of the disclosure, the FVIII molecule is full-length FVIII. The FVIII molecule is a protein which is encoded for by DNA sequences capable of hybridizing to DNA encoding FVIII:C. Such a protein may contain amino acid deletions at various sites between or within the domains A1-A2-B-A3-C1-C2 (U.S. Pat. No. 4,868,112). The FVIII molecule may also be an analog of native FVIII wherein one or more amino acid residues have been replaced by site-directed mutagenesis.

According to the present disclosure, the term "recombinant Factor VIII" (rFVIII) may include any rFVIII, heterologous or naturally occurring, obtained via recombinant DNA technology, or a biologically active derivative thereof. In certain embodiments, the term encompasses proteins as described above and nucleic acids, encoding a rFVIII of the disclosure. Such nucleic acids include, for example and without limitation, genes, pre-mRNAs, mRNAs, polymorphic variants, alleles, synthetic and naturally-occurring mutants. Proteins embraced by the term rFVIII include, for example and without limitation, those proteins and polypeptides described hereinabove, proteins encoded by a nucleic acid described above, interspecies homologs and other polypeptides that: (1) have an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity, over a region of at least about 25, about 50, about 100, about 200, about 300, about 400, or more amino acids (up to the full length sequence of 406 amino acids for the mature native protein), to a polypeptide encoded by a referenced nucleic acid or an amino acid sequence described herein; and/or (2) specifically bind to antibodies, e.g., polyclonal or monoclonal antibodies, generated against an immunogen comprising a referenced amino acid sequence as described herein, an immunogenic fragment thereof, and/or a conservatively modified variant thereof.

As used herein, "endogenous FVIII" includes FVIII which originates from the mammal intended to receive treatment. The term also includes FVIII transcribed from a transgene or any other foreign DNA present in said mammal. As used herein, "exogenous FVIII" includes FVIII which does not originate from said mammal.

The FVIII molecule exists naturally and in therapeutic preparations as a heterogeneous distribution of polypeptides arising from a single gene product (see, e.g., Andersson et al., Proc. Natl. Acad. Sci. USA, 83, 2979 2983, May 1986). The term "Factor VIII" as used herein refers to all such polypeptides, whether derived from blood plasma or produced through the use of recombinant DNA techniques and include, but is not limited too FVIII mimetics, fc-FVIII conjugates, FVIII chemically modified with water soluble polymers and other forms or derivatives of FVIII. Commercially available examples of therapeutic preparations containing FVIII include those sold under the trade names of HEMOFIL M and RECOMBINATE (available from Baxter Healthcare Corporation, Deerfield, Ill., U.S.A.). Other preparations comprise primarily a single subpopulation of FVIII molecules, which lack the B domain portion of the molecule.

The starting material of the present disclosure is FVIII, which can be derived from human plasma, or produced by recombinant engineering techniques, as described in patents U.S. Pat. Nos. 4,757,006; 5,733,873; 5,198,349; 5,250,421; 5,919,766; EP 306 968.

The FVIII molecules useful for the present disclosure include the full-length protein, precursors of the protein, biologically active or functional subunits or fragments of the protein, and functional derivatives thereof, as well as variants thereof as described herein below. Reference to FVIII is meant to include all potential forms of such proteins and wherein each of the forms of FVIII has at least a portion or all of the native B domain sequence intact.

Polynucleotides encoding a rFVIII of the disclosure include, without limitation, those that (1) specifically hybridize under stringent hybridization conditions to a nucleic acid encoding a referenced amino acid sequence as described herein, and conservatively modified variants thereof; (2) have a nucleic acid sequence that has greater than about 95%, about 96%, about 97%, about 98%, about 99%, or higher nucleotide sequence identity, over a region of at least about 25, about 50, about 100, about 150, about 200, about 250, about 500, about 1000, or more nucleotides (up to the full length sequence of 1218 nucleotides of the mature protein), to a reference nucleic acid sequence as described herein.

Variant (or analog) polypeptides include insertion variants, wherein one or more amino acid residues are added to an FVIII amino acid sequence of the disclosure. Insertions may be located at either or both termini of the protein, and/or may be positioned within internal regions of the FVIII amino acid sequence. Insertion variants, with additional residues at either or both termini, include for example, fusion proteins and proteins including amino acid tags or other amino acid labels. In one aspect, the FVIII molecule may optionally contain an N-terminal Met, especially when the molecule is expressed recombinantly in a bacterial cell such as E. coli.

In deletion variants, one or more amino acid residues in a FVIII polypeptide as described herein are removed. Deletions can be effected at one or both termini of the FVIII polypeptide, and/or with removal of one or more residues within the FVIII amino acid sequence. Deletion variants, therefore, include all fragments of a FVIII polypeptide sequence.

In substitution variants, one or more amino acid residues of a FVIII polypeptide are removed and replaced with alternative residues. In one aspect, the substitutions are conservative in nature and conservative substitutions of this type are well known in the art. Alternatively, the disclosure embraces substitutions that are also non-conservative. Exemplary conservative substitutions are described in Lehninger, [Biochemistry, 2nd Edition; Worth Publishers, Inc., New York (1975), pp. 71-77] and set out immediately below.

| CONSERVATIVE SUBSTITUTIONS | |
|---|---|
| SIDE CHAIN CHARACTERISTIC | AMINO ACID |
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

| CONSERVATIVE SUBSTITUTIONS II | |
|---|---|
| ORIGINAL RESIDUE | EXEMPLARY SUBSTITUTION |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

A "naturally-occurring" polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the disclosure can be recombinant molecules (e.g., heterologous and encoding the wild type sequence or a variant thereof, or non-naturally occurring). Reference polynucleotide and polypeptide sequences include, e.g., UniProtKB/Swiss-Prot P00451 (FA8_HUMAN); Gitschier J et al., Characterization of the human Factor VIII gene, Nature, 312(5992): 326-30 (1984); Vehar G H et al., Structure of human Factor VIII, Nature, 312 (5992):337-42 (1984); and Thompson A R. Structure and Function of the Factor VIII gene and protein, Semin Thromb Hemost, 2003:29; 11-29 (2002), (references incorporated herein in their entireties).

As used herein "biologically active derivative" or "biologically active variant" includes any derivative or variant of a molecule having substantially the same functional and/or biological properties of said molecule, such as binding properties, and/or the same structural basis, such as a peptidic backbone or a basic polymeric unit.

As used herein, "plasma-derived FVIII" or "plasmatic" includes all forms of the protein found in blood obtained from a mammal having the property of activating the coagulation pathway.

In various aspects, production of rFVIII includes any method known in the art for (i) the production of recombinant DNA by genetic engineering, (ii) introducing recombinant DNA into prokaryotic or eukaryotic cells by, for example and without limitation, transfection, electroporation or microinjection, (iii) cultivating said transformed cells, (iv) expressing rFVIII, e.g. constitutively or upon induction, and (v) isolating said rFVIII, e.g. from the culture medium or by harvesting the transformed cells, in order to (vi) obtain purified rFVIII.

In other aspects, the rFVIII is produced by expression in a suitable prokaryotic or eukaryotic host system characterized by producing a pharmacologically acceptable rFVIII molecule. Examples of eukaryotic cells are mammalian cells, such as CHO, COS, HEK 293, BHK, SK-Hep, and HepG2.

In still other aspects, a wide variety of vectors are used for the preparation of the rFVIII and are selected from eukaryotic and prokaryotic expression vectors. Examples of vectors for prokaryotic expression include plasmids such as, and without limitation, pRSET, pET, and pBAD, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as and without limitation pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and β-actin.

"International Unit," or "IU," is a unit of measurement of the blood coagulation activity (potency) of FVIII as measured by a standard assay such as a one stage assay. One stage assays are known to the art, such as that described in N Lee, Martin L, et al., An Effect of Predilution on Potency Assays of FVIII Concentrates, Thrombosis Research (Pergamon Press Ltd.) 30, 511 519 (1983). Another standard assay is a chromogenic assay. Chromogenic assays may be purchased commercially, such as the Coatest Factor VIII, available from Chromogeix AB, Molndal, Sweden.

The term "anneal" shall be used to indicate a step in the lyophilization process of a pharmaceutical preparation undergoing lyophilization, prior to the drying stages of the preparation, in which the temperature of the frozen preparation is raised from a lower temperature to a higher temperature and then cooled again after a period of time.

Bulking agents are those chemical entities which provide structure to the "cake" or residual solid mass of a pharmaceutical preparation after it has been lyophilized and which protect it against collapse. A crystallizable bulking agent shall mean a bulking a gent as described herein which can be crystallized during lyophilization, other than sodium chloride. HES is not included in this group of crystallizable bulking agents.

Freeze-drying, unless otherwise indicated by the context in which it appears, shall be used to denote the portion of a lyophilization process in which the temperature of a pharmaceutical preparation is raised in order to drive water out of the preparation. The "freezing" steps of a lyophilization process are those steps which occur prior to the freeze-drying stage. "Lyophilizing," unless otherwise indicated, shall refer to the entire process of lyophilization, including both the freezing steps and the freeze-drying steps.

Unless otherwise noted, percentage terms express weight/volume percentages and temperatures are in the Celsius scale.

Formulation and Lyophilization Development

In order to achieve maximal stability, the FVIII compositions of the present disclosure are, in one aspect, lyophilized. During lyophilization, FVIII is converted from being in an aqueous phase to being in an amorphous solid phase, which is thought to protect the protein from chemical and/or conformational instability. The lyophilized preparation not only contains an amorphous phase, but also includes a component which crystallizes during lyophilization. The inclusion of such a component is thought to allow the rapid lyophilization of the FVIII composition and the formation of a more elegant cake (that is, a cake with retention of cake structure and minimal shrinkage from the sides of the container in which it was lyophilized). In the formulations of the present disclosure, the stabilizing agents have been selected to exist in an amorphous phase of the lyophilized product, while the bulking agents (except HES) have been selected to crystallize during freezing.

Both the FVIII and the stabilizer are, in one aspect, dispersed in the amorphous phase of the lyophilized cake. The mass of the stabilizer is also, in one aspect, large compared to the other excipients in the amorphous form. In addition, the apparent glass transition temperature (Tg') of the amorphous phase is, in one aspect, relatively high during freeze-drying, and the glass transition temperature (Tg) of the solid is likewise preferably high during storage. Crystallization of sodium chloride in the product was found to be desirable, since amorphous sodium chloride will depress the Tg' of the amorphous phase.

In order to avoid the collapse of the cake of a particular composition, primary drying is, in one aspect, carried out at a product temperature below the apparent glass transition temperature of the freeze concentrate. An increase in drying time may also be required to offset a decrease in Tg'. Further information on lyophilization may be found in Carpenter, J. F. and Chang, B. S., Lyophilization of Protein Pharmaceuticals, Biotechnology and Biopharmaceutical Manufacturing, Processing and Preservation, K. E. Avis and V. L. Wu, eds. (Buffalo Grove, Interpharm Press, Inc.), pp. 199 264 (1996), U.S. Pat. Nos. 7,247,707, 7,087,723, 6,586573.

Lyophilization is carried out using techniques common in the art and should be optimized for the composition being developed [Tang et al., Pharm Res. 21:191-200, (2004) and Chang et al., Pharm Res. 13:243-9 (1996)].

A lyophilization cycle is, in one aspect, composed of three steps: freezing, primary drying, and secondary drying [A. P. Mackenzie, Phil Trans R Soc London, Ser B, Biol 278:167 (1977)]. In the freezing step, the solution is cooled to initiate ice formation. Furthermore, this step induces the crystallization of the bulking agent. The ice sublimes in the primary drying stage, which is conducted by reducing chamber pressure below the vapor pressure of the ice, using a vacuum and introducing heat to promote sublimation. Finally, adsorbed or bound water is removed at the secondary drying stage under reduced chamber pressure and at an elevated shelf temperature. The process produces a material known as a lyophilized cake. Thereafter the cake can be reconstituted with either sterile water or suitable diluent for injection.

The lyophilization cycle not only determines the final physical state of excipients but also affects other parameters such as reconstitution time, appearance, stability and final moisture content. The composition structure in the frozen state proceeds through several transitions (e.g., glass transitions and crystallizations) that occur at specific temperatures and the structure may be used to understand and optimize the lyophilization process. Tg and/or Tg' can provide information about the physical state of a solute and can be determined by differential scanning calorimetry (DSC). Tg and Tg' are an important parameter that must be taken into account when designing the lyophilization cycle. For example, Tg' is important for primary drying. Furthermore, in the dried state, the glass transition temperature provides information on likely acceptable storage temperatures for the final product.

In addition to the active drug, formulation components, in one aspect, include stabilizers, a surfactant, buffers, and a bulking agent in the case of a low dose drug. Special components addressing the unique needs of the protein, such as $Ca^{+2}$ with FVIII, are also be included, in various aspects. Many additives, such as sugars, glycerol, certain amino acids and amines all may serve as stabilizers. Stability is often rationalized in terms of "glass dynamics" that is, the formulation should form a 'non-reactive' amorphous solid, or glass, during freeze-drying, in which the protein is molecularly dispersed and coupled to the immobile glassy matrix such that mobility of the protein and potential reactants are greatly restricted. Immobilization means stabilization, at least qualitatively, since any degradation process will require molecular mobility of some type. The glassy matrix of the frozen concentrates and the dried amorphous phase are characterized by their glass transition temperatures, $T_g'$ and $T_g$, respectively. Below the glass transition temperature, mobility becomes very limited, and conversely, much above the glass transition, mobility becomes sufficiently high to support rapid chemical and physical degradation processes. As a general rule, the product temperature ($T_p$) during primary drying must be controlled near or below $T_g'$ ($T_p < T_g'$) to avoid collapse of an amorphous matrix during freeze drying (i.e., avoid an undesirable physical change) and be kept below $T_g$ during storage to avoid rapid degradation. However, simply storing below $T_g$ does not necessarily insure acceptable stability. Disaccharides have properties that allow them to function as both effective water substitutes and good glass formers. Typically, sucrose and trehalose, are used as stabilizers.

As described herein, a bulking agent is another important excipient in a protein formulation. A bulking agent's function is to provide "elegance" and more important, to protect product from "blow-out." That is, in the case of a low-dose drug, the drug concentration may be so small that the resulting dried product, or cake, has little mechanical strength. Thus, the momentum transfer from the flowing water vapor may disintegrate the cake and transfer pieces of the product out of the vial into the drying chamber. Typically, soluble, easily crystallized materials with high eutectic temperatures function well as bulking agents because they are easy to freeze dry without damage due to collapse. Mannitol and glycine are commonly employed in pharmaceutical products. The bulking agent needs to be present as the major component to insure essentially complete crystallization.

Formulations and Excipients in General

Excipients are additives that either impart or enhance manufacturability and/or final product quality, such as the stability and delivery of a drug product (e.g., protein). Regardless of the reason for their inclusion, excipients are an integral component of a formulation and therefore need to be safe and well tolerated by patients. For protein drugs, the choice of excipients is particularly important because they can affect both efficacy and immunogenicity of the drug. Hence, protein formulations need to be developed with appropriate selection of excipients that afford suitable stability, safety, and marketability.

A lyophilized formulation is, in one embodiment, at least comprised of one or more of a buffer, a bulking agent, and a stabilizer. In this embodiment, the utility of a surfactant is evaluated and selected in cases where aggregation during the lyophilization step or during reconstitution becomes an issue. An appropriate buffering agent is included to maintain the formulation within stable zones of pH during manufacturing (e.g. dilution, sterile filtration, filling, etc) and after reconstitution of the lyophilized product. A comparison of the excipient components contemplated for liquid and lyophilized protein formulations is provided in the following table:

| Excipient components of lyophilized protein formulations | |
| --- | --- |
| Excipient component | Function in lyophilized formulation |
| Buffer | Maintain pH of formulation during processing and upon reconstitution |
| stabilizer | Stabilizers include cryo and lyoprotectants Examples include Polyols, sugars and polymers Cryoprotectants protect proteins from freezing stresses Lyoprotectants stabilize proteins in the freeze-dried state |
| Bulking agent | Used to enhance product elegance and to prevent blowout Provides structural strength to the lyo cake Examples include mannitol and glycine |
| Surfactant | Employed if aggregation during the lyophilization process is an issue May serve to reduce reconstitution times Examples include polysorbate 20 and 80 |

-continued

Excipient components of lyophilized protein formulations

| Excipient component | Function in lyophilized formulation |
| --- | --- |
| Anti-oxidant | Oxidation reactions in the lyo cake are greatly retarded |
| Metal ions/ chelating agent | May be included if a specific metal ion is included only as a co-factor or where the metal is required for protease activity Chelating agents are generally not needed in lyo formulations, but may be used to retard metal ion catalyzed oxidations |
| Preservative | For multi-dose formulations only Provides protection against microbial growth in formulation Is usually included in the reconstitution diluent (e.g. bWFI) |

The principal challenge in developing formulations for proteins is stabilizing the product against the stresses of manufacturing, shipping and storage. The role of formulation excipients is to provide stabilization against these stresses. Excipients are also employed to reduce viscosity of high concentration protein formulations in order to enable their delivery and enhance patient convenience. In general, stabilizers can be classified on the basis of the mechanisms by which they stabilize proteins against various chemical and physical stresses. Some stabilizers are used to alleviate the effects of a specific stress or to regulate a particular susceptibility of a specific protein. Other stabilizers have more general effects on the physical and covalent stabilities of proteins. The stabilizers described herein are organized either by their chemical type or their functional role in formulations. Brief descriptions of the modes of stabilization are provided when discussing each stabilizer type.

Given the teachings and guidance provided herein, those skilled in the art will know what amount or range of excipient can be included in any particular formulation to achieve a biopharmaceutical formulation of the disclosure that is likely to promote retention in stability of the biopharmaceutical (e.g., a protein).

Of course, a person having ordinary skill in the art would recognize that the concentrations of the excipients described herein share an interdependency within a particular formulation. By way of example, the concentration of a bulking agent is, in one aspect, lowered where, e.g., there is a high protein concentration or where, e.g., there is a high stabilizing agent concentration. In addition, a person having ordinary skill in the art would recognize that, in order to maintain the isotonicity of a particular formulation in which there is no bulking agent, the concentration of a stabilizing agent could be increased accordingly (i.e., a "tonicifying" amount of stabilizer would be used). Common excipients are known in the art and can be found in Powell et al., Compendium of Excipients fir Parenteral Formulations (1998), PDA J. Pharm. Sci. Technology, 52:238-311.

Buffers and Buffering Agents

The stability of a pharmacologically active protein formulation is usually observed to be maximal in a narrow pH range. This pH range of optimal stability needs to be identified early during pre-formulation studies. Several approaches, such as accelerated stability studies and calorimetric screening studies, are useful in this endeavor (Remmele R. L. Jr., et al., Biochemistry, 38(16): 5241-7 (1999)). Once a formulation is finalized, the protein must be manufactured and maintained throughout its shelf-life. Hence, buffering agents are almost always employed to control pH in the formulation.

The buffer capacity of the buffering species is maximal at a pH equal to the pKa and decreases as pH increases or decreases away from this value. Ninety percent of the buffering capacity exists within one pH unit of its pKa. Buffer capacity also increases proportionally with increasing buffer concentration.

Several factors need to be considered when choosing a buffer. First and foremost, the buffer species and its concentration need to be defined based on its pKa and the desired formulation pH. Equally important is to ensure that the buffer is compatible with the protein and other formulation excipients, and does not catalyze any degradation reactions. A third important aspect to be considered is the sensation of stinging and irritation the buffer may induce upon administration. For example, citrate is known to cause stinging upon injection (Laursen T, et al., Basic Clin Pharmacol Toxicol., 98(2): 218-21 (2006)). The potential for stinging and irritation is greater for drugs that are administered via the subcutaneous (SC) or intramuscular (IM) routes, where the drug solution remains at the site for a relatively longer period of time than when administered by the IV route where the formulation gets diluted rapidly into the blood upon administration. For formulations that are administered by direct IV infusion, the total amount of buffer (and any other formulation component) needs to be monitored. One has to be particularly careful about potassium ions administered in the form of the potassium phosphate buffer, which can induce cardiovascular effects in a patient (Hollander-Rodriguez J C, et al., Am. Fam. Physician., 73(2): 283-90 (2006)).

Buffers for lyophilized formulations need additional consideration. Some buffers like sodium phosphate can crystallize out of the protein amorphous phase during freezing resulting in shifts in pH. Other common buffers such as acetate and imidazole may sublime or evaporate during the lyophilization process, thereby shifting the pH of formulation during lyophilization or after reconstitution.

In one embodiment, the buffer system present in the compositions is selected to be physiologically compatible and to maintain a desired pH of the pharmaceutical formulation. In another embodiment, the pH of the solution is between pH 2.0 and pH 12.0. For example, in various embodiments the pH of the solution may be 2.0, 2.3, 2.5, 2.7, 3.0, 3.3, 3.5, 3.7, 4.0, 4.3, 4.5, 4.7, 5.0, 5.3, 5.5, 5.7, 6.0, 6.3, 6.5, 6.7, 7.0, 7.3, 7.5, 7.7, 8.0, 8.3, 8.5, 8.7, 9.0, 9.3, 9.5, 9.7, 10.0, 10.3, 10.5, 10.7, 11.0, 11.3, 11.5, 11.7, or 12.0.

The pH buffering compound may be present in any amount suitable to maintain the pH of the formulation at a predetermined level. When appropriately low levels of buffer are used, crystallization and pH shift may be avoided. In one embodiment, the pH buffering concentration is between 0.1 mM and 500 mM (1 M). For example, it is contemplated that the pH buffering agent is at least 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 25, 30, 40, 50, 60, 70, 80, 90, 100, 200, or 500 mM.

Exemplary pH buffering agents used to buffer the formulation as set out herein include, but are not limited to organic acids, glycine, histidine, glutamate, succinate, phosphate, acetate, citrate, Tris, HEPES, and amino acids or mixtures of amino acids, including, but not limited to aspartate, histidine, and glycine. In one embodiment of the present disclosure, the buffering agent is histidine.

Stabilizers and Bulking Agents

In one embodiment of the present pharmaceutical formulations, a stabilizer (or a combination of stabilizers) is added to prevent or reduce storage-induced aggregation and chemical degradation. A hazy or turbid solution upon reconstitution normally indicates that the protein has precipitated or at least aggregated. The term "stabilizer" means an excipient capable of preventing aggregation, or chemical degradation (for example, autolysis, deamidation, oxidation, etc.). In certain embodiments, stabilizers contemplated include, but are not limited to, sucrose, trehalose, mannose, maltose, lactose, glucose, raffinose, cellobiose, gentiobiose, isomaltose, arabinose, glucosamine, fructose, mannitol, sorbitol, glycine, arginine HCL, poly-hydroxy compounds, including polysaccharides such as dextran, starch, hydroxyethyl starch, cyclodextrins, N-methyl pyrollidene, cellulose and hyaluronic acid, sodium chloride, calcium chloride [Carpenter et al., Develop. Biol. Standard 74:225, (1991)]. In one embodiment of the disclosure, trehalose is used as a stabilizing agent. In another embodiment of the disclosure, sucrose is used as a stabilizing agent. In the present formulations, the stabilizer is incorporated, in certain embodiments, in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM. Likewise, in certain embodiments of the disclosure, the stabilizer is incorporated in a concentration of about 0.005, 0.01, 0.02, 0.03, 0.05, 0.06, 0.07, 0.08, 0.09, 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, or 20% w/v.

If desired, the formulations also include appropriate amounts of bulking and osmolarity regulating agents. In various embodiments of the disclosure, bulking agents include, for example and without limitation, mannitol, glycine, sucrose, polymers such as dextran, polyvinylpyrolidone, carboxymethylcellulose, lactose, sorbitol, trehalose, or xylitol. In one embodiment, the bulking agent is mannitol. The bulking agent is incorporated, in various embodiments of the disclosure, in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM.

Surfactants

Proteins have a high propensity to interact with surfaces making them susceptible to adsorption and denaturation at air-liquid, vial-liquid, and liquid-liquid (silicone oil) interfaces. This degradation pathway has been observed to be inversely dependent on protein concentration and results in either the formation of soluble and insoluble protein aggregates or the loss of protein from solution via adsorption to surfaces. In addition to container surface adsorption, surface-induced degradation is exacerbated with physical agitation, as would be experienced during shipping and handling of the product.

Surfactants are commonly used in protein formulations to prevent surface-induced degradation. Surfactants are amphipathic molecules with the capability of out-competing proteins for interfacial positions (and/or promote proper refolding of a structurally altered protein molecule). Hydrophobic portions of the surfactant molecules occupy interfacial positions (e.g., air/liquid), while hydrophilic portions of the molecules remain oriented towards the bulk solvent. At sufficient concentrations (typically around the detergent's critical micellar concentration), a surface layer of surfactant molecules serve to prevent protein molecules from adsorbing at the interface. Thereby, surface-induced degradation is minimized. Surfactants contemplated herein include, without limitation, fatty acid esters of sorbitan polyethoxylates, i.e. polysorbate 20 and polysorbate 80. The two differ only in the length of the aliphatic chain that imparts hydrophobic character to the molecules, C-12 and C-18, respectively. Accordingly, polysorbate-80 is more surface-active and has a lower critical micellar concentration than polysorbate-20.

Detergents can also affect the thermodynamic conformational stability of proteins. Non-ionic surfactants are generally useful in protein stabilization. Ionic surfactants (detergents) normally destabilize proteins. Here again, the effects of a given detergent excipient will be protein specific. For example, polysorbates have been shown to reduce the stability of some proteins and increase the stability of others. Detergent destabilization of proteins can be rationalized in terms of the hydrophobic tails of the detergent molecules that can engage in specific binding with partially or wholly unfolded protein states. These types of interactions could cause a shift in the conformational equilibrium towards the more expanded protein states (i.e. increasing the exposure of hydrophobic portions of the protein molecule in complement to binding polysorbate). Alternatively, if the protein native state exhibits some hydrophobic surfaces, detergent binding to the native state may stabilize that conformation.

Another aspect of polysorbates is that they are inherently susceptible to oxidative degradation. Often, as raw materials, they contain sufficient quantities of peroxides to cause oxidation of protein residue side-chains, especially methionine. The potential for oxidative damage arising from the addition of stabilizer emphasizes the point that the lowest effective concentrations of excipients should be used in formulations. For surfactants, the effective concentration for a given protein will depend on the mechanism of stabilization.

Surfactants are also added in appropriate amounts to prevent surface related aggregation phenomenon during freezing and drying [Chang, B, J. Pharm. Sci. 85:1325, (1996)]. Thus, exemplary surfactants include, without limitation, anionic, cationic, nonionic, zwitterionic, and amphoteric surfactants including surfactants derived from naturally-occurring amino acids. Anionic surfactants include, but are not limited to, sodium lauryl sulfate, dioctyl sodium sulfosuccinate and dioctyl sodium sulfonate, chenodeoxycholic acid, N-lauroylsarcosine sodium salt, lithium dodecyl sulfate, 1-octanesulfonic acid sodium salt, sodium cholate hydrate, sodium deoxycholate, and glycodeoxycholic acid sodium salt. Cationic surfactants include, but are not limited to, benzalkonium chloride or benzethonium chloride, cetylpyridinium chloride monohydrate, and hexadecyltrimethylammonium bromide. Zwitterionic surfactants include, but are not limited to, CHAPS, CHAPSO, SB3-10, and SB3-12. Non-ionic surfactants include, but are not limited to, digitonin, Triton X-100, Triton X-114, TWEEN-20, and TWEEN-80. Surfactants also include, but are not limited to lauromacrogol 400, polyoxyl 40 stearate, polyoxyethylene hydrogenated castor oil 10, 40, 50 and 60, glycerol monostearate, polysorbate 40, 60, 65 and 80, soy lecithin and other phospholipids such as dioleyl phosphatidyl choline (DOPC), dimyristoylphosphatidyl glycerol (DMPG), dimyristoylphosphatidyl choline (DMPC), and (dioleyl phosphatidyl glycerol) DOPG; sucrose fatty acid ester, methyl cellulose and carboxymethyl cellulose. Compositions comprising these surfactants, either individually or as a mixture in different ratios, are therefore further provided. In one embodiment of the present disclosure, the surfactant is TWEEN-80. In the present formulations, the surfactant is incorporated in a concentration of about 0.01 to about 0.5 g/L. In formulations provided, in various embodiments, the surfactant concentration is 0.005, 0.01, 0.02, 0.03, 0.05, 0.06, 0.07, 0.08, 0.09, 0.1, 0.2, 0.3, 0.4, 0.5, 0.6, 0.7, 0.8, 0.9 or 1.0 g/L. Likewise, in certain embodiments of the disclosure, the surfactant is incorporated in a concentration of about 0.001, 0.002, 0.003, 0.004, 0.005, 0.01, 0.02, 0.03, 0.05, 0.06, 0.07, 0.08, 0.09, 0.1, 0.5, 0.7, 0.8 0.9, or 1.0% w/v.

Salts

Salts are often added to increase the ionic strength of the formulation, which can be important for protein solubility, physical stability, and isotonicity. Salts can affect the physical stability of proteins in a variety of ways. Ions can stabilize the native state of proteins by binding to charged residues on the protein's surface. Alternatively, salts can stabilize the denatured state by binding to peptide groups along the protein backbone (—CONH—). Salts can also stabilize the protein native conformation by shielding repulsive electrostatic interactions between residues within a protein molecule. Salts in protein formulations can also shield attractive electrostatic interactions between protein molecules that can lead to protein aggregation and insolubility. Salts (i.e., electrolytes) generally significantly depress the Tg', thereby making it more difficult, and sometimes impossible, to freeze dry the formulation. For this reason, only sufficient salt to maintain protein structural stability should be included in the formulation, and normally this level of electrolyte is very low.

In certain embodiments, the salt concentration of the formulations is between 0.0 (i.e., no salt), 0.001, 0.002, 0.003, 0.004, 0.005, 0.006, 0.007, 0.008, 0.009, 0.010, 0.011, 0.012, 0.013, 0.014, 0.015, 0.020, 0.050, 0.080, 0.1, 1, 10, 20, 30, 40, 50, 80, 100, 120, 150, 200, 300, and 500 mM. In one embodiment of the disclosure, 0.0 mM NaCl (i.e., no NaCl) is included in the formulation. One of skill in the art would appreciate that while NaCl is omitted or removed according to various embodiments of the present disclosure, trace amounts of NaCl may be present (i.e., due to the limitations of NaCl removal via dialysis or chromatography procedures). Thus, in various embodiments, "excluding NaCl" means that NaCl was never added to the formulation, and "trace amount of NaCl" means NaCl was removed from the formulation (e.g., to the extent possible by dialysis, solvent exchange chromatography, and the like).

Other Common Excipient Components

Amino Acids

Amino acids have found versatile use in protein formulations as buffers, bulking agents, stabilizers and antioxidants. Thus, in one aspect histidine and glutamic acid are employed to buffer protein formulations in the pH range of 5.5-6.5 and 4.0-5.5 respectively. The imidazole group of histidine has a pKa=6.0 and the carboxyl group of glutamic acid side chain has a pKa of 4.3 which makes these amino acids suitable for buffering in their respective pH ranges. Glutamic acid is particularly useful in such cases. Histidine is commonly found in marketed protein formulations, and this amino acid provides an alternative to citrate, a buffer known to sting upon injection. Interestingly, histidine has also been reported to have a stabilizing effect, with respect to aggregation when used at high concentrations in both liquid and lyophilized presentations (Chen B, et al., *Pharm Res.*, 20(12): 1952-60 (2003)). Histidine was also observed by others to reduce the viscosity of a high protein concentration formulation. However, in the same study, the authors observed increased aggregation and discoloration in histidine containing formulations during freeze-thaw studies of the antibody in stainless steel containers. Another note of caution with histidine is that it undergoes photo-oxidation in the presence of metal ions (Tomita M, et al., *Biochemistry*, 8(12): 5149-60 (1969)). The use of methionine as an antioxidant in formulations appears promising; it has been observed to be effective against a number of oxidative stresses (Lam X M, et al., *J Pharm Sci.*, 86(11): 1250-5 (1997)).

In various aspects, formulations are provided which include one or more of the amino acids glycine, proline, serine, arginine and alanine have been shown to stabilize proteins by the mechanism of preferential exclusion. Glycine is also a commonly used bulking agent in lyophilized formulations. Arginine has been shown to be an effective agent in inhibiting aggregation and has been used in both liquid and lyophilized formulations.

In formulations provided, the amino acid concentration is between 0.1, 1, 10, 20, 30, 40, 50, 80, 100, 120, 150, 200, 300, and 500 mM. In one embodiment of the present disclosure, the amino acid is glycine.

Antioxidants

Oxidation of protein residues arises from a number of different sources. Beyond the addition of specific antioxidants, the prevention of oxidative protein damage involves the careful control of a number of factors throughout the manufacturing process and storage of the product such as atmospheric oxygen, temperature, light exposure, and chemical contamination. The disclosure therefore contemplates the use of the pharmaceutical antioxidants including, without limitation, reducing agents, oxygen/free-radical scavengers, or chelating agents. Antioxidants in therapeutic protein formulations are, in one aspect, water-soluble and remain active throughout the product shelf-life. Reducing agents and oxygen/free-radical scavengers work by ablating active oxygen species in solution. Chelating agents such as EDTA are effective by binding trace metal contaminants that promote free-radical formation. For example, EDTA was utilized in the liquid formulation of acidic fibroblast growth factor to inhibit the metal ion catalyzed oxidation of cysteine residues. In one embodiment of the disclosure, glutathione is included in the formulation. In various embodiments of the formulations provided herein, the antioxidant concentration is 0.005, 0.01, 0.02, 0.03, 0.05, 0.06, 0.07, 0.08, 0.09, 0.1, 0.2, 0.3, 0.4, 0.5, 0.6, 0.7, 0.8, 0.9 or 1.0 mg/mL.

In addition to the effectiveness of various excipients to prevent protein oxidation, the potential for the antioxidants themselves to induce other covalent or physical changes to the protein is of concern. For example, reducing agents can cause disruption of intramolecular disulfide linkages, which can lead to disulfide shuffling. In the presence of transition metal ions, ascorbic acid and EDTA have been shown to promote methionine oxidation in a number of proteins and peptides (Akers M J, and Defelippis M R. Peptides and Proteins as Parenteral Solutions. In: Pharmaceutical Formulation Development of Peptides and Proteins. Sven Frokjaer, Lars Hovgaard, editors. Pharmaceutical Science. Taylor and Francis, UK (1999)); Fransson J. R., *J. Pharm. Sci.* 86(9): 4046-1050 (1997); Yin J, et al., *Pharm Res.*, 21(12): 2377-83 (2004)). Sodium thiosulfate has been reported to reduce the levels of light and temperature induced methionine-oxidation in rhuMab HER2; however, the formation of a thiosulfate-protein adduct was also reported in this study (Lam X M, Yang J Y, et al., *J Pharm Sci.* 86(11): 1250-5 (1997)). Selection of an appropriate antioxidant is made according to the specific stresses and sensitivities of the protein. Antioxidants contemplated in certain aspects include, without limitation, reducing agents and oxygen/ free-radical scavengers, metal complexing agents such as EDTA, and sodium thiosulfate.

Metal Ions

In general, transition metal ions are undesired in protein formulations because they can catalyze physical and chemical degradation reactions in proteins. However, specific metal ions are included in formulations when they are co-factors to proteins and in suspension formulations of proteins where they form coordination complexes (e.g., zinc suspension of insulin). Recently, the use of magnesium ions (10-120 mM) has been proposed to inhibit the isomerization of aspartic acid to isoaspartic acid (WO 2004039337).

Two examples where metal ions confer stability or increased activity in proteins are human deoxyribonuclease (rhDNase,PULMOZYME®), and FVIII. In the case of rhDNase, $Ca^{+2}$ ions (up to 100 mM) increased the stability of the enzyme through a specific binding site (Chen B, et al., *J Pharm Sci.*, 88(4): 477-82(1999)). In fact, removal of calcium ions from the solution with EDTA caused an increase in deamidation and aggregation. However, this effect was observed only with $Ca^{+2}$ ions; other divalent cations $Mg^{+2}$, $Mn^{+2}$ and $Zn^{+2}$ were observed to destabilize rhDNase. Similar effects were observed in FVIII. $Ca^{+2}$ and $Sr^{+2}$ ions stabilized the protein while others like $Mg^{+2}$, $Mn^{+2}$ and $Zn^{+2}$, $Cu^{+2}$ and $Fe^{+2}$ destabilized the enzyme (Fatouros A., et al., *Int. J Pharm.*, 155, 121-131(1997). In a separate study with FVIII, a significant increase in aggregation rate was observed in the presence of $Al^{+3}$ ions (Derrick TS, et al., J Pharm. Sci., 93(10): 2549-57(2004)).

Preservatives

Preservatives are necessary when developing multi-use parenteral formulations that involve more than one extraction from the same container. Their primary function is to inhibit microbial growth and ensure product sterility throughout the shelf-life or term of use of the drug product. Commonly used preservatives include, without limitation, benzyl alcohol, phenol and m-cresol. Although preservatives have a long history of use, the development of protein formulations that includes preservatives can be challenging. Preservatives almost always have a destabilizing effect (aggregation) on proteins, and this has become a major factor in limiting their use in multi-dose protein formulations (Roy S, et al., J Pharm Sci., 94(2): 382-96 (2005)). When practical, preservatives should be included in the diluent formulation and not included in the formulation to be freeze dried.

To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. ® (liquid, Novo Nordisk), NUTROPIN AQ® (liquid, Genentech) & Genotropin (lyophilized -dual chamber cartridge, Pharmacia & Upjohn) contain phenol while SOMA-TROPE® (Eli Lilly) is formulated with m-cresol.

Several aspects need to be considered during the formulation development of preserved dosage forms. The effective preservative concentration in the drug product must be optimized. This requires testing a given preservative in the dosage form with concentration ranges that confer antimicrobial effectiveness without compromising protein stability. For example, three preservatives were successfully screened in the development of a liquid formulation for interleukin-1 receptor (Type I), using differential scanning calorimetry (DSC). The preservatives were rank ordered based on their impact on stability at concentrations commonly used in marketed products (Remmele R L Jr., et al., *Pharm Res.*, 15(2): 200-8 (1998)).

Development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein significantly minimizing the associated stability risks. With liquid formulations, preservative effectiveness and stability have to be maintained over the entire product shelf-life (~18-24 months). An important point to note is that preservative effectiveness has to be demonstrated in the final formulation containing the active drug and all excipient components.

Some preservatives can cause injection site reactions, which is another factor that needs consideration when choosing a preservative. In clinical trials that focused on the evaluation of preservatives and buffers in Norditropin, pain perception was observed to be lower in formulations containing phenol and benzyl alcohol as compared to a formulation containing m-cresol (Kappelgaard A. M., Horm Res. 62 Suppl 3:98-103 (2004)). Interestingly, among the commonly used preservative, benzyl alcohol possesses anesthetic properties (Minogue S C, and Sun D A., *Anesth Analg.*, 100(3): 683-6 (2005)). In various aspects the use of preservatives provide a benefit that outweighs any side effects.

Methods of Preparation

The present disclosure further contemplates methods for the preparation of pharmaceutical formulations.

The present methods comprise one or more of the following steps: adding a stabilizing agent as described herein to said mixture prior to lyophilizing, adding at least one agent selected from a bulking agent, an osmolarity regulating agent, and a surfactant, each of which as described herein, to said mixture prior to lyophilization.

The standard reconstitution practice for lyophilized material is to add back a volume of pure water or sterile water for injection (WFI) (typically, but not necessarily, equivalent to the volume removed during lyophilization), although dilute solutions of antibacterial agents are sometimes used in the production of pharmaceuticals for parenteral administration [Chen, Drug Development and Industrial Pharmacy, 18:1311-1354 (1992)]. Accordingly, methods are provided for preparation of reconstituted FVIII compositions comprising the step of adding a diluent to a lyophilized FVIII composition of the disclosure.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

Administration

To administer compositions to human or test animals, in one aspect, the compositions comprises one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

The pharmaceutical formulations are administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions are carried out with the dose levels and pattern being selected by the treating physician. For the prevention or treatment of disease, the appropriate dosage depends on the type of disease to be treated, as defined above, the severity and course of the disease, whether drug is administered for preventive or therapeutic purposes, previous therapy, the patient's clinical history and response to the drug, and the discretion of the attending physician.

Kits

As an additional aspect, the disclosure includes kits which comprise one or more lyophilized compositions packaged in a manner which facilitates their use for administration to subjects. In one embodiment, such a kit includes pharmaceutical formulation described herein (e.g., a composition comprising a therapeutic protein or peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (i.e., almost none). In one embodiment, the kit contains a first container having a therapeutic protein or peptide composition and a second container having a physiologically acceptable reconstitution solution for the composition. In one aspect, the pharmaceutical formulation is packaged in a unit dosage form. The kit may further include a device suitable for administering the pharmaceutical formulation according to a specific route of administration. Preferably, the kit contains a label that describes use of the pharmaceutical formulations.

Dosages

The dosage regimen involved in a method for treating a condition described herein will be determined by the attending physician, considering various factors which modify the action of drugs, e.g. the age, condition, body weight, sex and diet of the patient, the severity of any infection, time of administration and other clinical factors. By way of example, a typical dose of a recombinant FVIII of the present disclosure is approximately 30 IU/kg to 50 IU/kg.

In one aspect, formulations of the disclosure are administered by an initial bolus followed by a continuous infusion to maintain therapeutic circulating levels of drug product. As another example, the inventive compound is administered as a one-time dose. Those of ordinary skill in the art will readily optimize effective dosages and administration regimens as determined by good medical practice and the clinical condition of the individual patient. The frequency of dosing depends on the pharmacokinetic parameters of the agents and the route of administration. The optimal pharmaceutical formulation is determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Such formulations influence the physical state, stability, rate of in vivo release, and rate of in vivo clearance of the administered agents. Depending on the route of administration, a suitable dose is calculated according to body weight, body surface area or organ size. Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

The following examples are not intended to be limiting but only exemplary of specific embodiments of the disclosure.

Example 1

Materials and Methods

Materials

The excipients used are analytical reagent grade. D-mannitol, trehalose, raffinose, sorbitol and sucrose were purchased from Pfanstiehl Lab. Inc. Glycine was obtained form Chattem Chemicals. M-hydroxyethyl starch, arginine, and alanine were obtained from Ajinomoto Co., Inc. Sodium chloride, calcium chloride and Tris base were obtained from Mallinckrodt Inc. Hepes, L-histidine and Polysorbate-80 were obtained from E. M. Science, Tanabe, Co. Inc. and Spectrum Int. Inc., respectively. Reduced glutathione was obtained from Sigma.

Formulation Preparation

The formulations described hereto were prepared using bulk drug substance (BDS), supplied by Baxter Healthcare Ltd. The BDS was composed of 3130 IU/ml rAHF (i.e., rFVIII); 50 mM Tris base, 0.4M NaCl, 0.1% polysorbate-80

(surfactant), 4 mM $CaCl_2$, pH 7. The $CaCl_2$ and surfactant are present to stabilize native conformation and reduce processing losses, respectively, and pH 7 was selected for optimal stability in solution, though other pH's would also provide optimal stability. The BDS was diluted by distilled water and mixed with various excipients to make a series of formulation solutions and neutralized to pH 7. Before filling into vials, the protein containing formulation solutions were filtered using 0.22µ pore size obtained from Millipore before filling (5 mL) into 30 cc, 20 mm finish Type I tubing vials. The vials and stoppers (Flurotec) were purchased from Daikyo Seiko.

Freeze Drying

Freeze-drying was conducted in a Dura-Stop/Dura-Dry or a LyoStar freeze-drier (FTS). Both freeze-dryers have 3 movable shelves, with total area of 4.0 and 4.6 sq. ft., respectively. Chamber pressure was measured using differential capacitance manometer (MKS). The product and shelf temperatures were measured via 30 gauge copper-constantan thermocouples placed bottom center in the vials, sampling the temperature of both edge and interior vials. Details of the different processes used are given in the appropriate results and discussion sections.

Potency Assay

The assay was carried out by using a COAG-A-MATE instrument (Organon Teknika Corp., Durham, N.C.). FVIII activity was determined by the one-stage activated partial thromboplastin time (APTT) assay, using human FVIII deficient plasma as a substrate and micronized silica as an activator. The FVIII potency was determined by testing two separate vials by two different analysts, each vial being tested in duplicate. Thus, the reported activity data were the average of the four replicate determinations. The average value was compared to the corresponding potency value sample stored at −70° C. and reported as percent of "−70° C. control". The usual standard deviation from replicate determinations was about 5%, meaning that the standard error in the mean was about 2.5%.

Water Content Assay

The moisture contents in the freeze-dried cakes were determined by Coulometric Karl Fisher titration, AF7LC (Fisher Scientific). The freeze-dried samples were suspended in 2 mL of previously dried methanol and shaken for about 5 minutes to ensure that the methanol did wet all the powder in the vial and formed a fine slurry. All 2 mL of the slurry was quickly transferred into the titrator to minimize exposure of the sample to the atmosphere. Using the same type of vials and stoppers, a number of blank runs were made with only methanol, following the same procedure as described above. The amount of water in the freeze-dried samples was calculated from the difference of sample and blank titre values. Every measurement was repeated three times by using three different vials. Reported water contents were the mean of the three measurements and were precise within ±0.1% or better.

Thermal Analysis

A TA Instruments Differential Scanning calorimetry (DSC-2920) was used to measure glass transition temperatures, $T_g$, of freeze-dried cakes and to measure the glass transition temperature of the freeze dried concentrate in frozen systems, $T_g'$ which is normally taken to represent the temperature slightly less than the collapse temperature, which is the maximum temperature normally recommended for primary drying. The DSC was operated at "modulated" mode under "all heating" conditions with an amplitude of 0.796° C., a period of 60 seconds, and a linear scan rate of 2° C./min. Dry samples were handled in a dry bag, which was continuously flushed with dry nitrogen gas to maintain relative humidity less than 2%. About 5-10 mg of freeze-dried samples were compacted into disks ~3-4 mm in thickness before sealing in the aluminum pans. For measurements on frozen solutions, about 50 µL solution was transferred into the Al DSC pan, and sealed. All DSC measurements were performed in a dry nitrogen atmosphere (50 mL/min.). Calibration of temperature and energy were made according to standard procedure using high purity of indium. Glass transitions were determined as the mid-point of the transition as given by the reversing signal and are reproducible within about ±0.5° C.

Freeze Drying Microscopy

Collapse temperature measurements were performed using freeze-drying microscopy. The sample is placed between two glass cover slips and frozen rapidly to a temperature below −50° C. The chamber containing the sample is evacuated to 200 mTorr, and the process of freeze-drying is observed through a microscope at increasing sample temperatures. Freeze drying with retention of "cake structure" in the dried region is observed below the collapse temperature. At a temperature above the collapse temperature, loss of structure in the dried region is observed. Collapse temperatures are reproducible within ±1° C.

X-Ray Powder Diffraction

X-ray powder diffraction studies employed a Norelco Powder Diffractometer with a CuKα source (λ=1.54 Å) operating at a tube load of 40 kv and 40 mA. The freeze-dried samples were gently ground to a fine powder, spread over the sampleholder, and gently pressed before loading. All scans were performed under ambient conditions of temperature and humidity. The samples were scanned from 10° to 60° (2☐) at a scan rate of 0.5°/minute.

Example 2

Since variation in the level of NaCl is generally not acceptable, particularly in a commercial product, and since crystallization of a component is generally facilitated by increased concentration of that component relative to the other components, it was decided to add NaCl to increase the level to a value above the highest level expected in the process and sufficiently high so that crystallization of NaCl during the freezing step would be possible. Modulated Differential Scanning calorimeter (MDSC) was used to study the freezing of various concentrations of sodium chloride in a formulation that further contained 0.02% (w/v) Polysorbate-80, 10 mM Tris, 4 mM calcium chloride, and 2% (w/v) sucrose. For this experiment, 200 mM sodium chloride was used. Other concentrations could be used, including, but not limited to those in the range of 1 mM to 10000 mM, or 10 mM to 1000 mM or 100 mM to 500 mM, or 150 mM to 300 mM to ensure that complete crystallization of the sodium chloride occurred during freezing.

In one preferred embodiment, samples containing 200 mM sodium chloride were used, resulting in a ($T_g'$) value of the frozen solid (−39° C.) that approached the $T_g'$ of the system in the absence of sodium chloride (−36° C.), suggesting that most of the sodium chloride had crystallized. Collapse temperatures (via freeze drying microscopy) were within about 1° C. of the $T_g'$ value. Solutions containing 150 mM or less sodium chloride gave $T_g'$ values less than −50° C., indicating the presence of uncrystallized sodium chloride (i.e. amorphous sodium chloride). This observation was confirmed in limited studies on material freeze dried in vials. When lyophilized, solutions containing less than 200 mM sodium chloride exhibited varying degrees of collapse in the cake structure, as predicted by the $T_g'$ data, but at >200 mM NaCl, collapse was avoided, and crystalline bulking agent and NaCl resulted (x-ray powder diffraction).

Example 3

The effect different concentrations of rAHF have on the stability of rAHF when the rAHF is exposed to stresses in different stages of freeze-drying was examined. Two samples containing different concentrations of rAHF, 600 and 60 IU/mL (corresponding to 150 & 15 µg/ml) were used without any stabilizer. The formulation composition for these samples was: 8% mannitol (bulking agent), 10 mM Tris buffer, 200 mM NaCl, 4 mM $CaCl_2$, 0.02% Polysorbate-80, pH 7.0. A third sample used a formulation that employed 2% sucrose as a stabilizer in addition to these components. The drying process used, described in Table 1, produces product temperatures of about −42° C., which is sufficiently low to prevent collapse in most formulations; though this process was not optimized.

TABLE 1

Freezing and lyophilization procedure for preliminary rAHF stability studies.

| Process step | Description |
| --- | --- |
| Freezing | Cool to +5° C., hold for 10 minutes |
| | Cool to −5° C. at 1° C./minute, hold for 20 minutes |
| | Cool to −20° C. at 1° C./minute, hold for 1 hr |
| | Cool to −45° C. at 0.5° C./minute, hold for 1 hr |
| | take 3 samples for potency assay |
| Frozen hold at −35° C. | Following "Freezing" |
| | Hold at −35° C. for 48 hrs |
| | Pull out 3 samples for potency assay |
| Frozen hold at both −35° C. and −20° C. | Following "Frozen hold at −35° C." |
| | Hold at −20° C. for 48 hr |
| | take 3 samples for potency assay |
| Freeze-dried | Following "Frozen hold at both −35° C. and −20° C." |
| | Cool to −45° C. at 0.5° C./minute, hold for 1 hr |
| | Set chamber pressure to 65 mTorr |
| | set shelf to −32° C.; primary drying for ≈ 55 hours. |
| | set shelf to +40° C. at 0.2° C./minute; hold for 3 hours secondary drying |
| | take 3 samples for potency assay |

The effect of concentration of the protein on in-process stability of rAHF was evaluated by pulling out small aliquots of each sample at each stage of the freeze-drying process (as described in Table 1) and determining the activity of rAHF. The results are summarized in Table 2.

TABLE 2

Stability of rAHF during Processing and Storage of Freeze Dried Solid at 40° C.: Preliminary Stability Study. Processing Details as given in Table 1. Uncertainty given for rate constants is standard error as provided by the regression analysis. Standard error in the % Loss data is about 3%. The rate constant, k, is defined by the "stretched time" kinetic expression,
Activity = (Activity, −70° control) · exp(−k · √t),
where time, t, is in months.

| | % Loss of rAHF activity during step or rate constant | | |
| --- | --- | --- | --- |
| Processing protocol, or step | Solution A, 600 IU/mL | Solution B 60 IU/mL | Solution C, 60 IU/mL, with Sucrose |
| Freezing | 3 | 35 | 39 |
| Frozen hold at −35° C. | 2 | 9 | 4 |
| Frozen hold at −35° C. and −20° C. | 7 | 12 | 5 |
| Drying | 20 | 24 | 18 |
| Storage Dry Solid @ 40° C., rate constant (k) | 1.34 ± 0.16 | 1.85 ± 0.17 | 0.45 ± 0.05 |

The formulations (samples B and C) containing the lower level of rAHF (60 IU/ml) lost 35-39% of initial rAHF potency during freezing, while the formulation (sample A) containing the higher rAHF (600 IU/ml) lost only about 3%. Note that the uncertainty in the data is about 3%; thus, loss of activity during freezing the high concentration formula was negligible. During the following thermal treatment and lyophilization, the formulation containing a higher concentration of rAHF also had a lower loss of activity than the formulation containing a lower concentration of rAHF and no sucrose. These observations suggest that higher concentrations of rAHF have a self-protection effect. The loss of activity during drying was significant (18-24%) and comparable for all formulations. Stability during storage was slightly better for the high concentration sample (A) than for the low concentration sample (B), and much better for the sucrose containing formulation sample (C).

Example 4

Formulation samples were screened for stability and freeze drying behavior to identify preferred formulations for rAHF. In one embodiment, the formulations involved various combinations of bulking agents (generally 8%) and stabilizers (2%), though the skilled artisan will recognize that other concentrations of bulking agents and stabilizers are similarly suitable. In this same embodiment, the formulations using hydroxyethyl starch (HES) or NaCl as bulking agents used them at concentrations of 4% and 2.3%, respectively, though again, the skilled artisan will recognize that other concentrations for these excipients are similarly suitable. In addition, all the formulations included the following excipients and conditions: 220 mM NaCl, 0.03% (v/v) polysorbate-80, 4 mM $CaCl_2$, 10 mM TRIS buffer, and pH 7. The freeze-drying cycle used the specific combinations of stabilizers and bulking agents described in Table 3.

TABLE 3

Freeze-drying cycle and formulations for stability screening studies. In each case the buffer system was: 220 mM NaCl, 0.03% (v/v) polysorbate-80, 4 mM CaCl$_2$, 10 mM Tris buffer, pH 7

| Freeze-drying cycle | Stabilizer (w/v) | Bulking agent (w/v) |
|---|---|---|
| Freezing: | 2% Sucrose | 8% Mannitol |
| 1. Ramp to −5° C. at 0.5° C./min, hold for ½ hr. | 2% Trehalose | 8% Mannitol |
| 2. Ramp to −22° C. at 0.5° C./min, hold for 3 hr. | 2% Raffinose | 8% Mannitol |
| 3. Ramp to −45° C. at 0.5° C./min, hold for 1 hr. | 2% Arginine | 8% Mannitol |
| Drying: | 2% Lysine | 8% Mannitol |
| 1. Set chamber pressure to 65 mTorr | 2% Sorbitol | 8% Mannitol |
| Ramp to −32° C. at 0.5° C./min; hold for 66.7 hr. | 2% Glycine | 8% Mannitol |
| Product temperatures ≈ −42° C. | 2% Sucrose | 4% HES |
| 2. Ramp to +40° C. at 0.2° C./min, hold for 3 hr. | 2% Sucrose | 8% Glycine |
| | 2% Trehalose | 8% Glycine |
| | 2% Sucrose | 2.34% NaCl |
| | 2% Sucrose | 8% Alanine |

All formulations contained 100 IU/ml rAHF in the initial solution. The lower level of rAHF was selected because the instability of rAHF would be maximized at a lower protein concentration, thus allowing easier evaluation of stability differences. Formulation screening to identify the potential formulation candidates used two sets of criteria, (1) physical characteristics and (2) stability.

Physical Characteristics: The physical characteristics of freeze-dried products were judged by the following criteria: (1) the ability to freeze dry without collapse to low residual moisture (usually <1%) within reasonable time, (2) the glass transition temperature of the freeze-dried solids, (3) the appearance of the freeze-dried product, and (4) the reconstitution time as determined by dissolving the vial contents in 5 mL of sterile water for injection. The results of the physical characterization are shown in Table 4.

TABLE 4

Physical characteristics of freeze-dried formulations from screening study. The term, "Elegant", means freeze drying without significant loss of cake structure.

| Sample I.D. | Water content (%) | Tg (° C.) | Reconstitution (s) | Appearance |
|---|---|---|---|---|
| Mannitol/sucrose | n/c | 54 | 64 | Acceptable |
| Mannitol/trehalose | 1.4 | 53 | 62 | Top partially collapsed |
| Mannitol/raffinose | 1.7 | 54 | 77 | Elegant |
| Mannitol/arginine | — | — | — | Partial collapsed |
| Mannitol/lysine | — | — | — | Total collapsed |
| Mannitol/sorbitol | 0.6 | <10° C. | 63 | Elegant |
| Mannitol/glycerol | — | <10° C. | — | Elegant |
| HES/sucrose | 0.7 | 86 | 49 | Elegant, but shrinkage |
| Glycine/sucrose | 0.8 | 54 | 22 | Elegant |
| Glycine/trehalose | — | 63 | 18 | Elegant |
| NaCl/sucrose | 0.4 | 66 | 11 | Elegant (layer on bottom) |
| Alan/sucrose | 0.5 | — | 57 | Elegant |

In general, all the freeze-dried solids had acceptable reconstitution time. However, all had higher residual moisture contents and lower glass transition temperatures than desired, especially the mannitol-based formulations. In addition, x-ray powder diffraction data (data not shown) showed evidence for mannitol hydrate peaks, indicating that some of the mannitol crystallized to the mannitol hydrate, which is difficult to desolvate. In addition, at least for mannitol containing systems, incomplete crystallization of mannitol will significantly lower the $T_g$ of the amorphous phase as the $T_g$ of amorphous mannitol is only about 13° C.

In-Process Stability: All the formulations except mannitol/lysine were prepared, filtered, filled and lyophilized using the process described in Table 3. The in-process stability was estimated by the recovery of rAHF potency from the initial formulation. FIG. 1 summarizes the percent activity of rAHF after processing in various formulations relative to the initial activity. The activity of rAHF in the mannitol/glycerol formulation was essentially totally lost (99.8% loss); therefore, data for this formulation are not shown in the figure. The activity of rAHF in the formulations containing mannitol/sorbitol and glycine/raffinose also suffered significant activity losses during processing. The poor in-process stability of rAHF in formulations containing glycerol and sorbitol is attributed to the very low glass transition temperatures, $T_g'$ (<−50° C.) of the frozen systems and the expected low $T_g$'s of the systems in secondary drying. The $T_g$ of sorbitol is −1.6° C. (20) and that for glycerol is even lower.

Storage Stability: The freeze-dried samples were placed on stability test at different temperatures (−70° C., 5° C., 25° C., 40° C. and 50° C., 60° C.) for selected times. At each time point, two vials of each sample were removed for activity assay. The activity of rAHF at each time point was normalized to the activity of control rAHF samples held at −70° C. This procedure insured that long-term variation in the assay was cancelled (no time dependence in the assay of samples stored at −70° was noted). As is common for degradation in amorphous solids, degradation followed "stretched time" kinetics and were fully consistent with the linear equation, $$P = P_O - k\sqrt{t} \qquad (1)$$

Where,
P=Activity of FVIII at time t
$P_o$=Initial potency of FVIII (=potency of the control at −70° C.)
k=Rate constant for degradation
t=time (in months)

Equation 1 is consistent with degradation from a multitude of independent microstates, not in equilibrium in the glassy state, each with different degradation rate. Thus, the rate constant (k) determined from equation 1 represents a combination of rate constants from a number of different protein configurations within the lyophilized matrix, each of which degrades at a different rate. In general, the rate equation is expected to involve the log of the activity being linear in time raised to some power less than unity, with that power frequently being ½, but in cases of low levels of degradation the linear equation (equation 1) is a valid approximation. In many samples degradation is not minimal, and indeed the preliminary data given in Table 2, where the extent of degradation was particularly large, did not fit equation 1 well and required the log expression. For several samples studied herein, a good fit could be obtained with the log version of equation 1, but the linear expression, equation crystallization has less serious impact on the $T_g'$ than does incomplete crystallization of glycine, a direct result of the much lower $T_g'$ for glycine than for mannitol.

Minimizing Oxidation: The Roles of Glutathione and Histidine

Oxidation is a pathway by which rAHF products lose functional activity. N-acetyl-L-cystine, lipoic acid, and/or reduced glutathione are suitable stabilizers for use in a preferred embodiment of the disclosure, with glutathione being the most effective antioxidant (data not shown). Accordingly, 0.2 mg/mL reduced glutathione was added to the formulations under study.

TABLE 5

Process, formulation, and physical characteristics for Mannitol:Trehalose based formulation with Histidine buffer and Glutathione antioxidant.

| Freeze-drying cycle | Formulation | Characteristics |
|---|---|---|
| Freezing: | Buffer: | Residual water: |
| 1. Ramp shelf at 0.5° C./min. to −5° C.; hold for ½ hr. | 25 mM Histidine | 0.2 ± 0.02% |
| | 0.2 g/L Glutathione | $T_g$: 69 ± 2° C. |
| 2. Ramp shelf at 0.5° C./min. to −40° C.; hold for 1 hr. | 0.03% Tween-80 | Elegant |
| | 225 mM NaCl | appearance |
| 3. Ramp shelf at 0.5° C./min. to −22° C.; hold for 3 hr. | 4 mM $CaCl_2 \cdot 2H_2O$ | |
| | PH = 7 | |
| 4. Ramp shelf at 0.5° C./min. to −55° C.; hold for 1.5 hr. | Formulation: | |
| | Buffer | |
| 5. Ramp shelf at 0.5° C./min. to −33° C.; hold for 4 hr. | +2% Trehalose | |
| | +8% Mannitol | |
| 6. Ramp shelf at 0.5° C./min. to −45° C.; hold for 1 hr. | +77.4 U/mL rAHF | |
| Drying | | |
| 1. Set chamber pressure to 65 mTorr, and ramp shelf at 0.5° C./min to −35° C.; hold for 90 hr. Product temperature ≈ −41° C. | | |
| 2. Ramp shelf at 0.2° C./min. to 40° C.; hold for 3 hr. | | |
| 3. Ramp shelf at 0.2° C./min. to 45° C.; hold for 3 hr. | | |
| 4. Ramp shelf at 0.2° C./min. to 50° C.; hold for 3 hr. | | |
| TOTAL CYCLE TIME: 113 hr | | |

Figure 2:
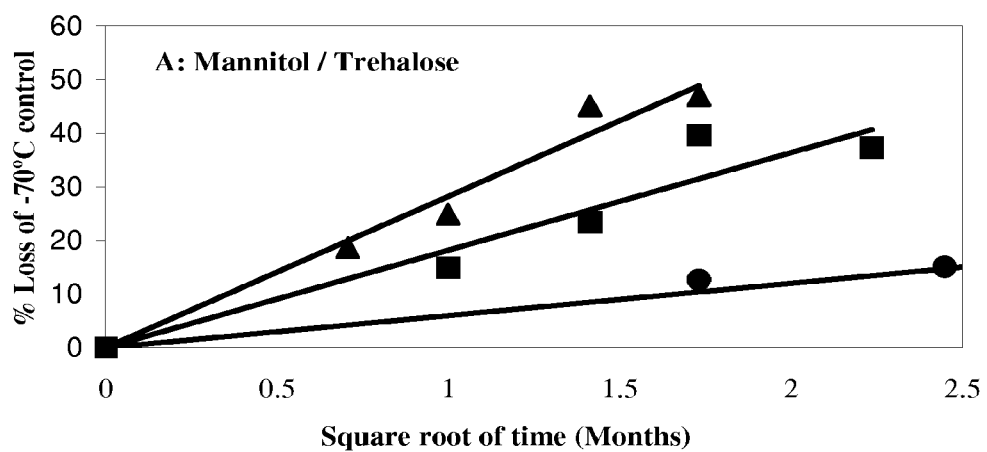
Figure 2:
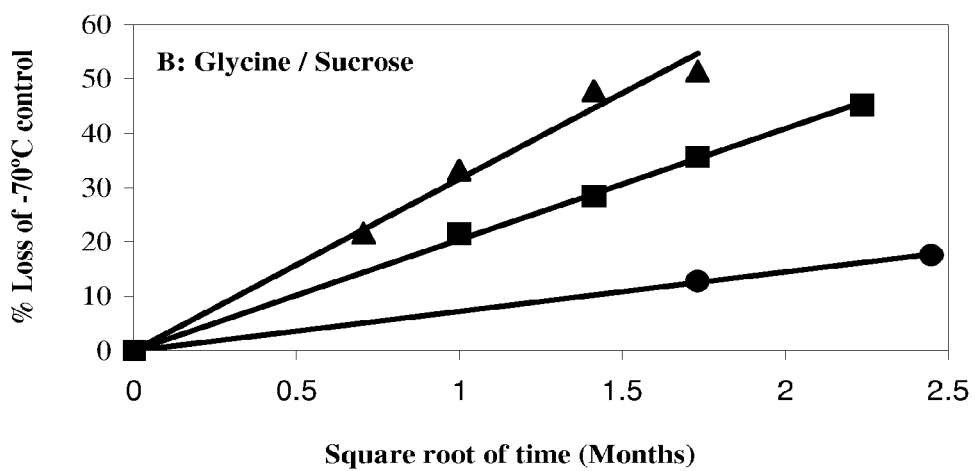

1, actually fit the data slightly better in nearly every case. Thus, empirically, the use of equation 1 is acceptable, and it is reasonable to compare rate constants derived from this expression. The suitability of equation 1 in representing the data is illustrated in FIG. 2 where the percent activity loss relative to the −70° C. control sample is plotted as a function of the square root of time for two formulations of rAHF stored at 25° C., 40° C. and 50° C. The linearity of the plotted results was excellent.

Figure 3:
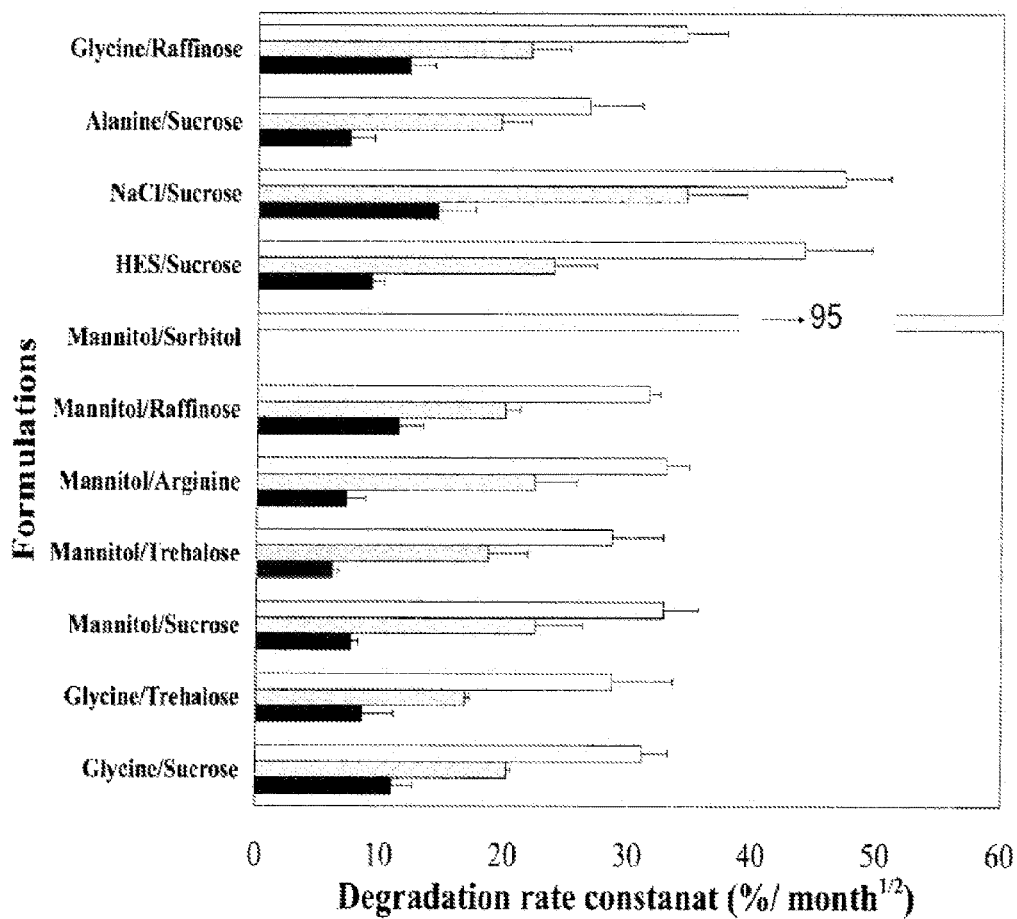
FIG. 3. Rate constants for degradation of freeze-dried rAHF in selected formulations: Formulation screening study.

The degradation rate constants of rAHF in the various formulations at 25° C., 40° C. and 50° C. were obtained by regression analysis, using equation 1, and are compared in FIG. 3. The results show that the NaCl based formulation was less stable than formulations that lack NaCl.

Selection of Final Candidate Formulations: The following formulations were subjected to further analysis due to their preferred characteristics: mannitol/arginine, glycine/trehalose and mannitol/trehalose. The mannitol/trehalose formulation comprises a preferred embodiment because it produces an elegant cake and trehalose has a very high glass transition temperature (−117° C.) and would therefore be less subject to glass transition temperature issues if residual water were to increase, as for example via absorption of water from the stoppers during storage. Furthermore, mannitol is easily crystallizable, and the lack of complete The studied formulations included one or more of the following buffers: TRIS, histidine and/or HEPES.

Figure 4:
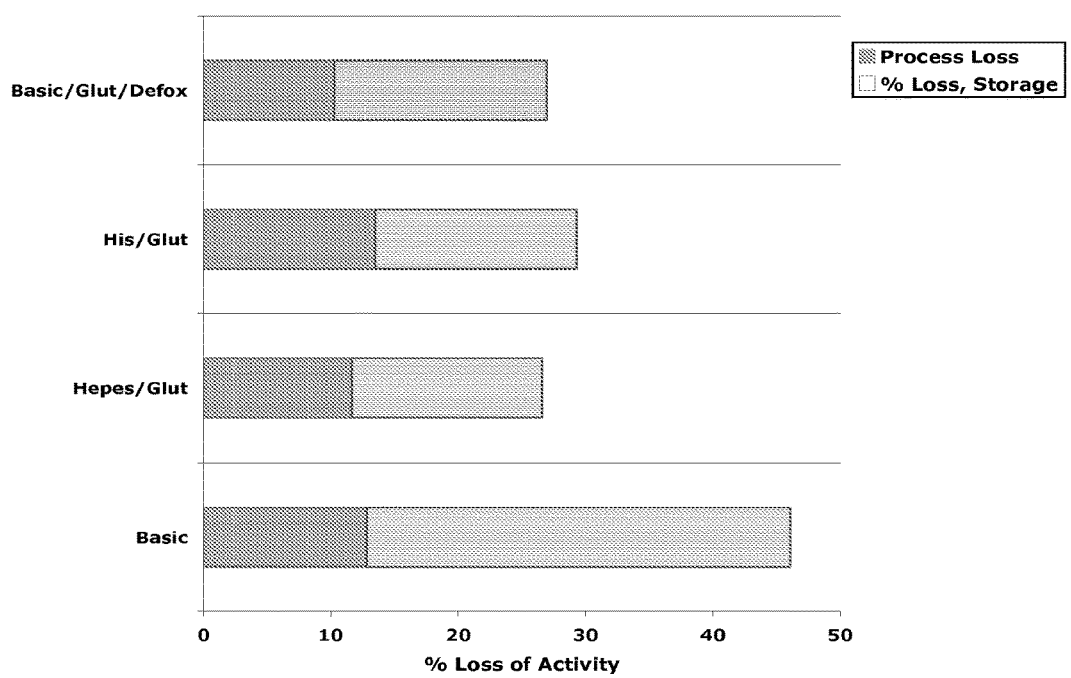
FIG. 4. The Effects of Glutathione, Histidine, and Hepes on Stability of Glycine:Trehalose Based Formulations: In-process loss of activity and loss of activity of during 9 months storage at 25° C. The "Basic" formulation is: rAHF (103 IU/mL), Glycine (8%), Trehalose (2%), NaCl (200 mM), 10 mM Tris, 0.025% polysorbate 80, 4 mM CaCl$_2$, at pH 7. The other formulations consist of the "Basic" formulation to which has been added glutathione (0.2 g/L) and either Hepes buffer (10 mM), Histidine buffer (50 mM), or the iron complexing agent Deferoxamine (0.25 mg/L). The process used was essentially the same as that given in Table 5.

Although the pKa of histidine is too low for optimal buffering at pH 7, histidine was attractive because it was speculated that histidine might act as an iron chelator, thereby limiting iron catalyzed oxidation. Another potential advantage of histidine over hepes is its inherent higher $T_g$ (37° C.) than HEPES (11° C.), thus contributing to a higher glass transition temperature in the final freeze-dried cakes. It is generally recognized that addition of glutathione improves storage stability, with the results shown in FIG. 4 being typical. In FIG. 4, a comparison is conducted regarding the loss on processing and loss during 9 months storage at 25° C. for four Glycine/Trehalose formulations. In-process degradation was essentially the same for all formulations. The "Basic" formulation, without either histidine or glutathione, was clearly the least stable during storage, but the other three formulations, all of which included glutathione, showed the same level of degradation during storage at 25° C. That is, either the "Basic" formulation plus the iron chelator, deferoxamine, or the "Basic" formulation plus 10 mM HEPES gave the same stability as the formulation with histidine.

A Simple Formulation Alternative: Disaccharide Only Formulations without NaCl

The freeze-drying characteristics and stability of formulations when the NaCl was removed was examined. NaCl was removed from the BDS by dialysis against a buffer without NaCl. The resulting BDS contained in one embodiment, trace amounts of NaCl and in another embodiment, no NaCl. The buffer compositions and the formulation compositions, as well as the physical characteristics of the freeze-dried products, and process used are given in Table 6.

Even using the non-optimized freeze-drying cycle, the excipient formulations where the NaCl was removed and no NaCl was added as an excipient during the preparation of the final formulation prior to lyophilization, especially the trehalose based formulation, provided products with extremely low residual moisture content and high $T_g$ values, all with a process that was substantially shorter than needed for formulations where NaCl was added as an excipient (83 hr vs 113 hr, see Tables 5 and 6).

TABLE 6

Process, Formulation, and physical characteristics for trehalose and sucrose based formulations without bulking agent or NaCl.

| Freeze-drying cycle | Formulations | Residual water, % | $T_g$ (° C.) |
|---|---|---|---|
| Freezing: | Buffer: | | |
| 1. Ramp shelf at 1.0° C./min. to −5° C.; hold for 20 min. | 25 mM Histidine 0.2 mg/ml Glutathione | | |
| 2. Ramp shelf at 1.0° C./min. to −43° C.; hold for 1 hr. | 0.03% Tween-80, 4 mM CaCl$_2$•2H$_2$O | | |
| Drying: | PH = 7 | | |
| 1. Set chamber pressure to 45 mTorr and ramp shelf at 1.0° C./min to −30° C.; hold for 70 hr. Product temperature ≈ −41° C. | Formulation 1: Buffer + 5% trehalose + 53.4 IU/ml rAHF | 0.05 ± 0.02 | 114 ± 2 |
| 2. Ramp shelf at 0.1° C./min. to 40° C.; hold for 4 hr. | Formualtion 2: Buffer + 5% sucrose + 54.2 IU/ml rAHF | 0.11 ± 0.01 | 80 ± 2 |
| 3. Ramp shelf at 0.1° C./min. to 45° C.; hold for 4 hr | | | |
| 4. Ramp shelf at 0.1° C./min. to 50° C.; hold for 4 hr | | | |
| TOTAL CYCLE TIME: 83 hr | | | |

Figure 5:
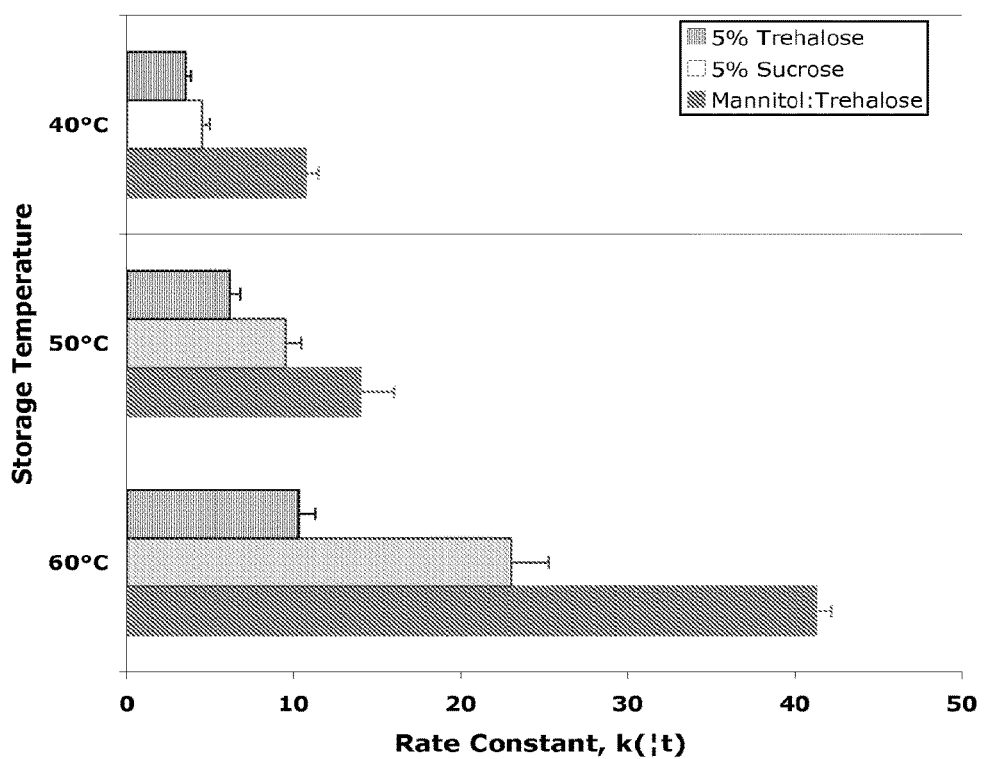
FIG. 5. Degradation rate constants of freeze-dried rAHF. Details of formulations and processes are given in Tables 5 and 6. Rate constant is from square root of time kinetics with time in months. Error bars represent standard errors as given by the regression analysis.

The storage stability of rAHF in the disaccharide only formulations where NaCl was removed from the BDS were compared with stability in a formulation where NaCl was at a minimum added to the BDS as an excipient as shown in FIG. 5. All the formulations contain glutathione and histidine and differ only in the presence of bulking agent (mannitol) and NaCl, as well as a slightly lower rAHF concentration in the disaccharide only formulation due to loss (or dilution) that occurred on dialysis. The formulations where the NaCl was removed and no NaCl was added to the BDS as an excipient during formulation, freeze dried more quickly than formulations where NaCl was added as an excipient and resulted in an elegant product. Additionally, the stability is significantly better without NaCl, particularly for the trehalose formulation at 40° and 60° C. Given the data in FIG. 5, and assuming Arrhenius behavior, the rate constant at 25° C. is 3.0 (time in months) for the NaCl containing formulation, while the corresponding rate constant for the trehalose only formulation is 1.44. This difference translates into a 4-year time period needed for the trehalose formulation without NaCl to degrade by 10% but only 11 months for the formulation that includes NaCl to degrade by 10%. In short, room temperature stability is a reality following the removal of NaCl by dialysis and not adding NaCl following dialysis as a formulation excipient, with the result that the lyophilization time-period is shortened.

Considering the above, in one embodiment of the disclosure a formulation is provided according to Table 6.

The invention claimed is:

1. A method of preparing a stable, lyophilized Factor VIII (FVIII) comprising the steps of:
    (a) preparing a formulation comprising
        (1) a FVIII; (2) one or more buffering agents; (3) one or more antioxidants; (4) one or more stabilizing agents; and (5) one or more surfactants;
    said FVIII comprising a polypeptide selected from the group consisting of:
        i) a recombinant FVIII polypeptide; and
        ii) a biologically active analog, fragment or variant of i);
    said buffer comprises a pH buffering agent in a range of about 0.1 mM to about 500 mM and said pH is in a range of about 2.0 to about 12.0;
    said antioxidant is at a concentration of about 0.005 to about 1.0 mg/ml;
    said stabilizing agent is at a concentration of about 0.005 to about 20% (w/v);
    said surfactant is at a concentration of about 0.001% to about 1.0% (w/v); and
    said formulation excluding sodium chloride (NaCl) as an excipient; and
    (b) lyophilizing the formulation of step (a).

2. The method according to claim 1 wherein stability of the lyophilized FVIII is higher compared to a FVIII formulation that is lyophilized in the presence of NaCl.

3. The method according to claim 1 wherein the buffering agent is selected from the group consisting of citrate, glycine, histidine, HEPES, Tris and combinations of these agents.

4. The method according to claim 3 wherein the buffering agent is histidine.

5. The method according to claim 1 wherein pH is in the range of about 6.0 to about 8.0.

6. The method according to claim 5 wherein pH is in the range of about 6.5 to about 7.5.

7. The method according to claim 1 wherein the buffering agent is histidine and the pH is about 7.0.

8. The method according to claim 1 wherein the antioxidant is selected from the group consisting of glutathione.

9. The method according to claim 8 wherein the antioxidant is at a concentration range of about 0.1 to about 0.5 mg/ml.

10. The method according to claim 9 wherein the antioxidant is glutathione at a concentration of about 0.2 mg/ml.

11. The method according to claim 1 wherein the buffering agent is histidine and the pH is about 7.0; and wherein the antioxidant is glutathione at a concentration of about 0.2 mg/ml.

12. The method according to claim 1 wherein the one or more stabilizing agents is selected from the group consisting of sucrose, trehalose, and raffinose, and combinations of these stabilizing agents.

13. The method according to claim 1 wherein the stabilizing agents are trehalose at a concentration of about 5% and calcium chloride at a concentration of about 4 mM.

14. The method according to claim 1 wherein the stabilizing agents are sucrose at a concentration of about 5% and calcium chloride at a concentration of about 4 mM.

15. The method according to claim 1 wherein the surfactant is selected from the group consisting of digitonin, Triton X-100, Triton X-114, TWEEN-20, TWEEN-80 and combinations of these surfactants.

16. The method according to claim 15 wherein the surfactant is TWEEN-80 at about 0.03%.

17. The method according to claim 1 wherein the buffering agent is histidine at a concentration of about 25 mM at about pH 7.0; wherein the antioxidant is glutathione at a concentration of about 0.2 mg/ml; wherein the stabilizing agents are trehalose or sucrose at a concentration of about 5% and calcium chloride at a concentration of about 4 mM; and wherein the surfactant is TWEEN-80 at about 0.03%.

18. The method according to claim 1, wherein
said buffer comprises a pH buffering agent in a range of about 0.1 mM to about 500 mM and said pH is in a range of about 2.0 to about 12.0;
said antioxidant is glutathione at a concentration of about 0.005 to about 1.0 mg/ml;
said stabilizing agent is trehalose or sucrose at a concentration of about 0.005 to about 20%; and
said surfactant is TWEEN-80 at a concentration of about 0.001% to about 1.0%.

19. The method according to claim 1, wherein
said buffer comprises a pH buffering agent in a range of about 0.1 mM to about 500 mM and said pH is in a range of about 2.0 to about 12.0;
said antioxidant is glutathione at a concentration of about 0.005 to about 1.0 mg/ml;
said stabilizing agent is trehalose at a concentration of about 0.005 to about 20%;
and said surfactant is TWEEN-80 at a concentration of about 0.001% to about 1.0%.

* * * * *